United States Patent
Michihata et al.

(10) Patent No.: US 11,980,348 B2
(45) Date of Patent: May 14, 2024

(54) MEDICAL CONTROL APPARATUS AND METHOD OF CONTROLLING MEDICAL CONTROL APPARATUS

(71) Applicant: Sony Olympus Medical Solutions Inc., Tokyo (JP)

(72) Inventors: Taihei Michihata, Tokyo (JP); Hiroshi Myoken, Tokyo (JP); Satoshi Mitsui, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 686 days.

(21) Appl. No.: 17/149,753

(22) Filed: Jan. 15, 2021

(65) Prior Publication Data
US 2021/0281731 A1 Sep. 9, 2021

(30) Foreign Application Priority Data

Mar. 3, 2020 (JP) .................. 2020-036302

(51) Int. Cl.
*G06T 7/62* (2017.01)
*A61B 1/00* (2006.01)
(Continued)

(52) U.S. Cl.
CPC .......... *A61B 1/045* (2013.01); *A61B 1/00006* (2013.01); *A61B 1/000095* (2022.02);
(Continued)

(58) Field of Classification Search
CPC ......... A61B 1/00002–00009; A61B 1/04–055; G02B 23/243; G02B 23/2415; G02B 7/001; G06T 2207/10068
See application file for complete search history.

(56) References Cited

U.S. PATENT DOCUMENTS 9,554,097 B2 * 1/2017 Sasaki ................ A61B 1/00174
10,485,629 B2 * 11/2019 Michihata ............... A61B 1/045
(Continued)

FOREIGN PATENT DOCUMENTS

JP   5976342 B2 * 8/2016
JP   2018138141 A   9/2018
(Continued)

OTHER PUBLICATIONS

Winter, Christian, et al. "Automatic adaptive enhancement for images obtained with fiberscopic endoscopes." IEEE Transactions on Biomedical Engineering 53.10 (2006): 2035-2046. (Year: 2006).*

*Primary Examiner* — Vu Le
*Assistant Examiner* — Charles C L Penny
(74) *Attorney, Agent, or Firm* — XSENSUS LLP

(57) ABSTRACT

A medical control apparatus to which a rigid endoscope having an insertion portion to be inserted into a subject is detachably connected is configured to perform image processing on a captured image obtained by capturing a subject image introduced by the rigid endoscope and generate a medical photographic image to be displayed on a display device that displays images. The medical control apparatus includes: a detection unit configured to detect a mask width that is a distance between boundary points dividing the subject image included in the captured image and a mask area that is an area other than the subject image; and a control unit configured to calculate a first parameter used for the image processing in accordance with the mask width.

20 Claims, 14 Drawing Sheets

(51) Int. Cl.

| | |
|---|---|
| *A61B 1/04* | (2006.01) |
| *A61B 1/045* | (2006.01) |
| *A61B 1/06* | (2006.01) |
| *G06T 7/13* | (2017.01) |
| *H04N 9/73* | (2023.01) |
| *H04N 23/71* | (2023.01) |
| *H04N 23/72* | (2023.01) |
| *H04N 23/50* | (2023.01) |

(52) U.S. Cl.
CPC ...... *A61B 1/00045* (2013.01); *A61B 1/00078* (2013.01); *A61B 1/00105* (2013.01); *A61B 1/042* (2013.01); *A61B 1/0669* (2013.01); *G06T 7/13* (2017.01); *G06T 7/62* (2017.01); *H04N 9/73* (2013.01); *H04N 23/71* (2023.01); *H04N 23/72* (2023.01); *A61B 1/00114* (2013.01); *A61B 1/00117* (2013.01); *G06T 2207/10068* (2013.01); *G06T 2207/30004* (2013.01); *H04N 23/555* (2023.01)

(56) References Cited

U.S. PATENT DOCUMENTS

| | | | |
|---|---|---|---|
| 10,918,265 B2* | 2/2021 | Watanabe | A61B 1/000095 |
| 2003/0076411 A1* | 4/2003 | Iida | H04N 7/183 |
| | | | 348/E7.087 |
| 2009/0231418 A1* | 9/2009 | Higuchi | G06T 3/40 |
| | | | 345/626 |
| 2011/0115980 A1* | 5/2011 | Shmueli | H04N 5/57 |
| | | | 348/E5.062 |
| 2017/0046833 A1 | 2/2017 | Lurie | |
| 2018/0027165 A1* | 1/2018 | Murakita | H04N 23/71 |
| | | | 348/68 |
| 2018/0242827 A1* | 8/2018 | Michihata | H04N 25/583 |
| 2018/0242830 A1* | 8/2018 | Michihata | A61B 1/00195 |
| 2020/0021746 A1* | 1/2020 | Tamonoki | G03B 13/36 |

FOREIGN PATENT DOCUMENTS

| | | |
|---|---|---|
| JP | 2019033917 A | 3/2019 |
| JP | 2019162280 A | 9/2019 |
| JP | 2020005844 A | 1/2020 |
| WO | WO-2020039716 A1 | 2/2020 |

* cited by examiner

FIG.5
(a)
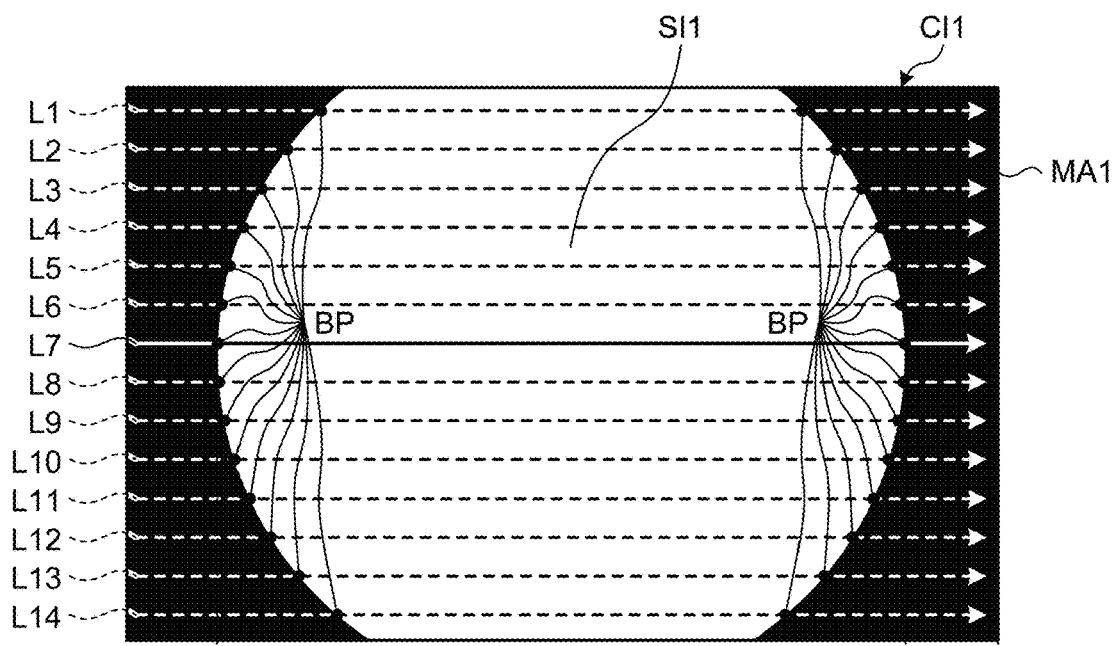
(b)
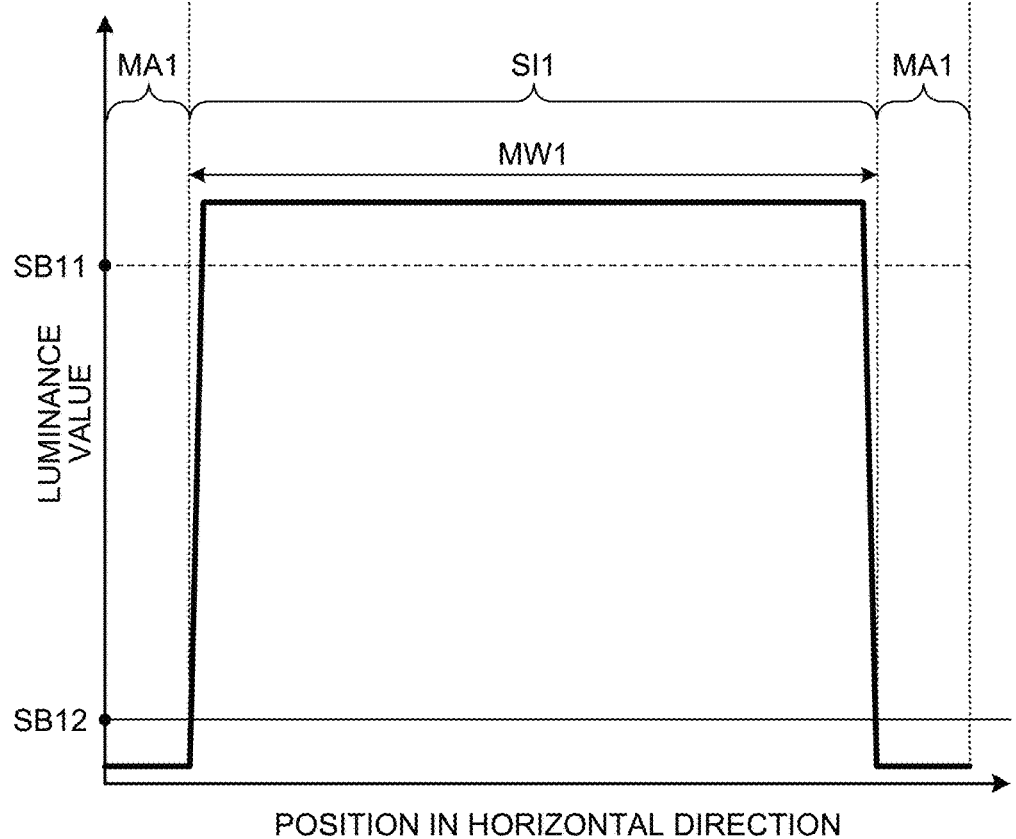
POSITION IN HORIZONTAL DIRECTION

FIG.6
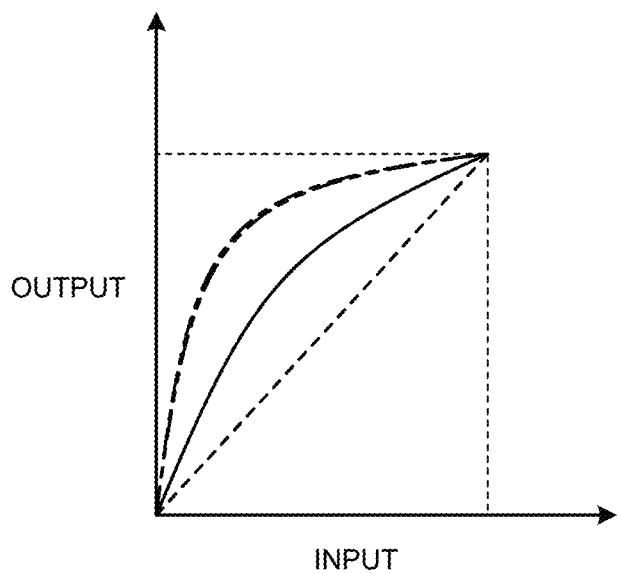
<GAMMA CORRECTION>
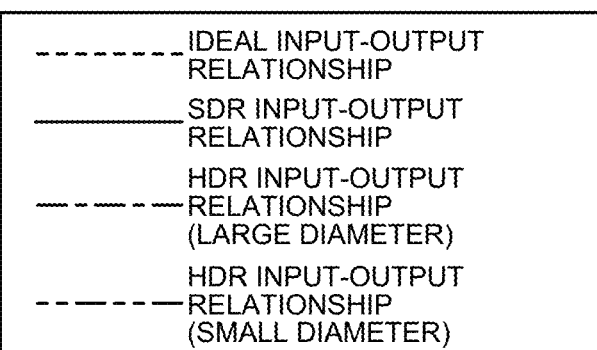

FIG.7
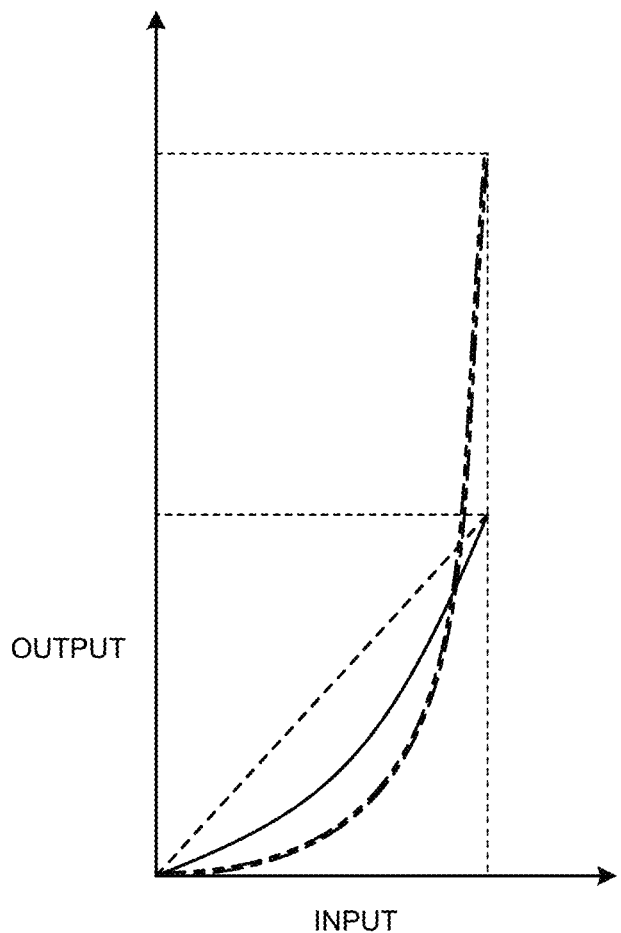
<INVERSE GAMMA CORRECTION>
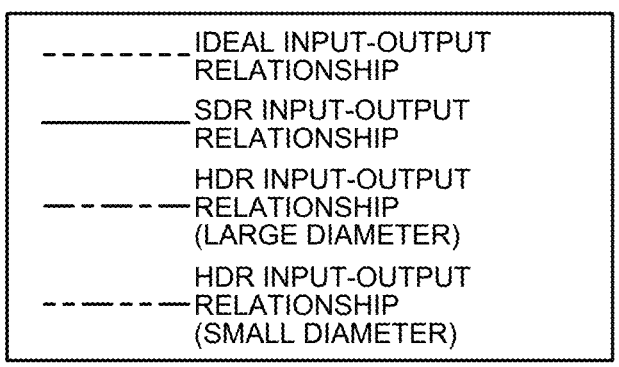

FIG.15
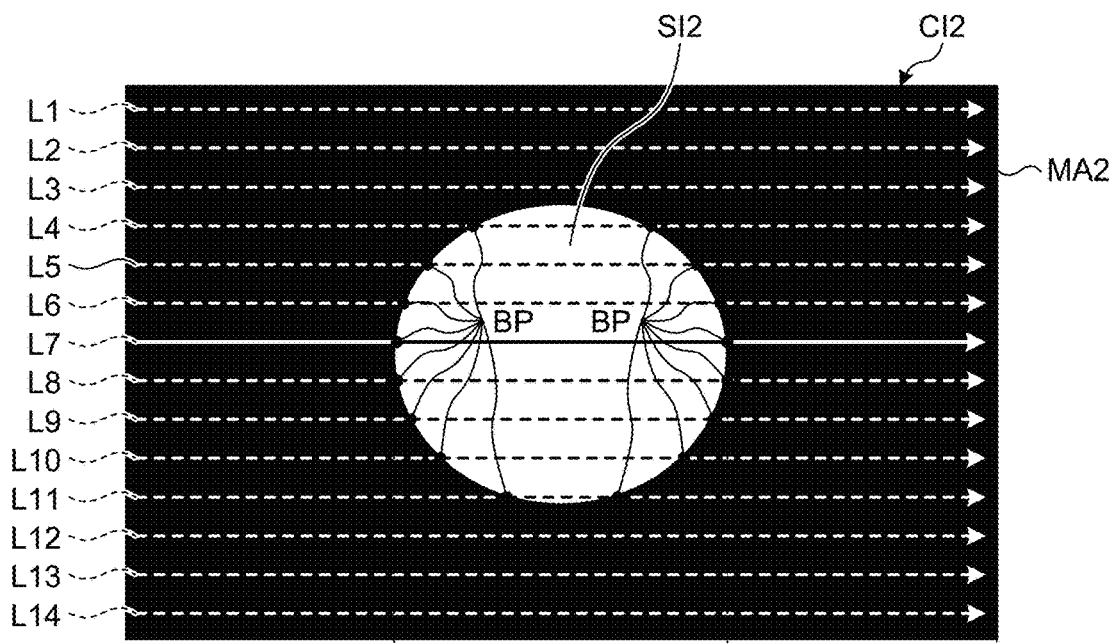
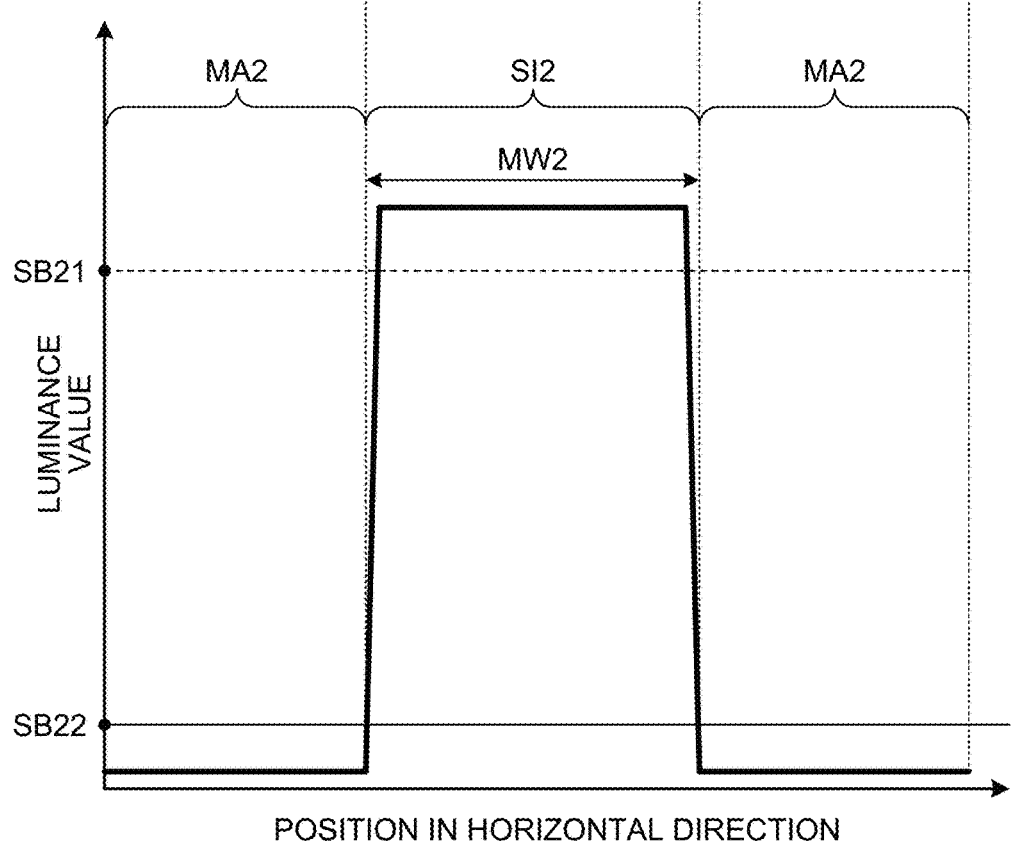

# MEDICAL CONTROL APPARATUS AND METHOD OF CONTROLLING MEDICAL CONTROL APPARATUS

CROSS-REFERENCE TO RELATED APPLICATION

This application claims priority from Japanese Application No. 2020-036302, filed on Mar. 3, 2020, the contents of which are incorporated by reference herein in its entirety.

BACKGROUND

The present disclosure relates to a medical control apparatus and a method of controlling a medical control apparatus.

In the medical field, there is known an endoscope apparatus in which a rigid endoscope is connected to a camera head and an insertion portion of the rigid endoscope is inserted into a patient's body or the like to image an observation target. When an image of an observation target is captured by the endoscope apparatus, there might be a case where forceps, gauze, or the like other than the observation target are imaged together with a subject image. In a case where the brightness of the captured image displayed on the display device does not match the brightness of the forceps or gauze, the brightness level of the image displayed on the display device will be higher as a whole in some cases. This might result in an occurrence of blown-out highlights in the displayed image, leading to loss of information and colors in a portion that the surgeon desires to observe.

In order to reduce the blown-out highlights, it is typically effective to expand a dynamic range of an image sensor. For example, using a large image sensor with a large cell size may be effective for expanding the dynamic range of the image sensor. This would make it possible to capture an image corresponding to a wide dynamic range, enabling the reduction of the blown-out highlights in the image displayed on a display device. Furthermore, in order to reduce blown-out highlights, it is also effective to perform high dynamic range (HDR) imaging that combines a plurality of low to high brightness images captured at different times with various shutter speeds at the time of imaging. This makes it possible to generate an image corresponding to a wide dynamic range, enabling the reduction of the blown-out highlights at display of the image.

For reference, JP 2002-135589 A below discloses a technique of optimizing the luminance of an arbitrary position in an image based on user's operation when converting a wide dynamic range image into a narrow dynamic range image.

SUMMARY

In an endoscope apparatus, miniaturization of the camera head is desired, and therefore, it is difficult to use a large image sensor. Moreover, an imaging method of generating an HDR image by combining two images, a long exposure image and a short exposure image would have a concern of occurrence of blurring in the image when the relative position between the subject and the image sensor changes. Therefore, this type of imaging method is not desirable to be used for an endoscope apparatus that observes internal portions of the body while moving the image sensors. In view of this, by controlling the brightness of the captured image so that the higher the dynamic range of the display device, the lower the brightness of the captured image, it is possible to reduce the blown-out highlights occurring when the brightness of the medical photographic image is increased and displayed on the display device.

Meanwhile, some endoscope apparatuses enable a plurality of different types of rigid endoscopes to be connected to the camera head. Depending on the types of the rigid endoscope, the amount of light introduced by the rigid endoscope differs due to the reason of the difference in the diameter of the insertion portion, or the like. The smaller amount of light introduced by the rigid endoscope connected to the camera head leads to the lower brightness of the captured image, making it necessary to increase the gain for the captured image.

Unfortunately, however, known control apparatuses in endoscopes have performed image processing on the captured image without consideration of the amount of light introduced by the rigid endoscope, causing a problem of difficulty in applying appropriate image processing on the captured image depending on the type of the rigid endoscope.

According to one aspect of the present disclosure, there is provided a medical control apparatus to which a rigid endoscope having an insertion portion to be inserted into a subject is detachably connected, the medical control apparatus being configured to perform image processing on a captured image obtained by capturing a subject image introduced by the rigid endoscope and generate a medical photographic image to be displayed on a display device that displays images, the medical control apparatus including: a detection unit configured to detect a mask width that is a distance between boundary points dividing the subject image included in the captured image and a mask area that is an area other than the subject image; and a control unit configured to calculate a first parameter used for the image processing in accordance with the mask width.

BRIEF DESCRIPTION OF THE DRAWINGS

FIG. 5 is a diagram illustrating a process of detecting a mask width;

FIG. 6 is a diagram illustrating an example of an input-output relationship in a medical control apparatus;

FIG. 7 is a diagram illustrating an example of an input-output relationship in a display device;

FIG. 15 is a diagram illustrating an example of a captured image when rigid endoscopes having different diameters of insertion portions are connected.

DETAILED DESCRIPTION

Figure 1:
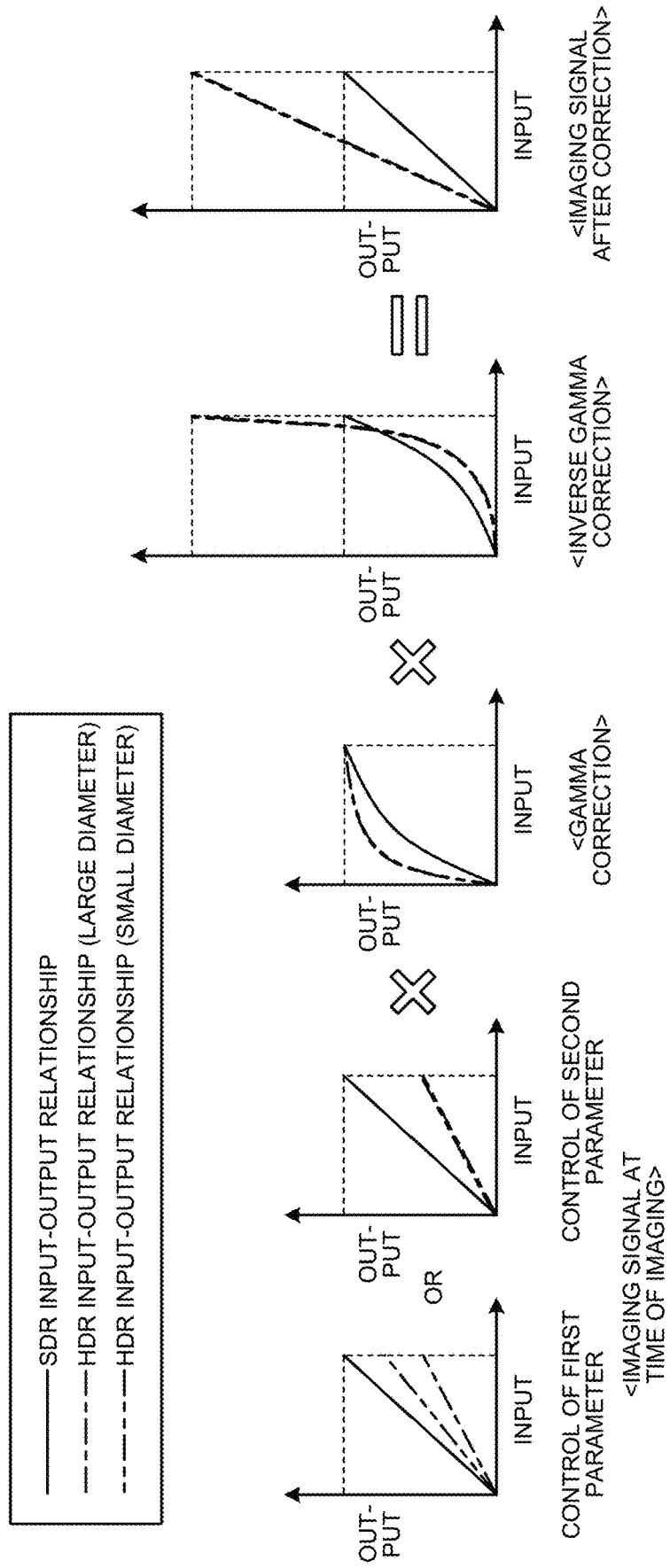
FIG. 1 is a diagram illustrating an outline of an embodiment.

Preferred embodiments of the present disclosure will be described in detail below with reference to the accompanying drawings. In the present specification and the drawings, components having substantially the same functional configuration are designated by the same reference numerals to omit duplicate description.

Embodiments

Overview Hereinafter, an outline of an embodiment will be described with reference to FIG. 1. FIG. 1 is a diagram illustrating an outline of the embodiment. The following describes an example in which a medical control apparatus according to the embodiment is applied to an endoscope apparatus used in a medical field. However, application targets of the medical control apparatus are not limited to the endoscope apparatus. For example, the medical control apparatus may be applied to a medical observation apparatus that uses an imaging device to image an observation target such as a patient from the outside.

When an endoscope apparatus images an observation target such as internal portions of a patient, the endoscope apparatus may include forceps, gauze, or the like other than the observation target in the subject in the imaging. In a case where the brightness of the captured image displayed on the display device does not match the brightness of the forceps or gauze, the brightness level of the image displayed on the display device will be higher as a whole in some cases. This might result in an occurrence of blown-out highlights in the displayed image, leading to loss of information and colors in a portion that the surgeon desires to observe.

In order to reduce the blown-out highlights, it is typically effective to expand a dynamic range of an image sensor. For example, using a large image sensor with a large cell size may be effective for expanding the dynamic range of the image sensor. This would make it possible to capture an image corresponding to a wide dynamic range, enabling the reduction of the blown-out highlights in the image displayed on a display device. Furthermore, in order to reduce blown-out highlights, it is also effective to perform high dynamic range (HDR) imaging that combines a plurality of low to high brightness images captured at different times with various shutter speeds at the time of imaging. This makes it possible to generate an image corresponding to a wide dynamic range, enabling the reduction of the blown-out highlights at display of the image.

However, miniaturization of the camera head is desired in an endoscope apparatus, and it makes difficult to use a large image sensor. Moreover, an imaging method of generating an HDR image by combining two images, a long exposure image and a short exposure image would have a concern of occurrence of blurring in the image when the relative position between the subject and the image sensor changes. Therefore, this type of imaging method is not desirably to be used for an endoscope apparatus that observes internal portions of the body while moving the image sensors.

Therefore, the medical control apparatus controls the brightness of the captured image so that the higher the dynamic range of the display device, the lower the brightness of the captured image. This is because the display device having a higher dynamic range may display the medical photographic image with higher brightness, and in addition, higher the brightness, the higher the possibility of occurrence of blown-out highlights in a displayed medical photographic image. The medical control apparatus decreases the brightness at the time of imaging the observation target in accordance with the brightness of the medical photographic image to be displayed on the display device, enabling reduction of the blown-out highlights occurring in a case where the medical photographic image is displayed in higher brightness on the display device.

In the embodiment, the display device indicating a high dynamic range is a high dynamic range (HDR) display device having a high dynamic range. Here, the HDR display device is a display device having a maximum displayable luminance of an image being 1000 nits or more. In contrast, the display device indicating a lower dynamic range is a standard dynamic range (SDR) display device having a standard dynamic range. Here, the SDR display device is a display device having a maximum displayable luminance of an image being less than 1000 nits. The type of display device based on the dynamic range is not limited to the HDR display device and the SDR display device described above, and may be display devices based on other dynamic ranges. The following describes an example in which a display device on which the medical photographic image is displayed is either an HDR display device or an SDR display device.

In addition, some endoscope apparatuses enable a plurality of different types of rigid endoscopes to be connected to the camera head. Depending on the types of the rigid endoscope, the amount of light introduced by the rigid endoscope differs due to the reason of the difference in the diameter of the insertion portion, or the like.

In the embodiment, the brightness of the captured image is controlled so that the higher the dynamic range of the display device, the lower the brightness of the captured image, and furthermore, the amount of light introduced by the insertion portion is detected by the mask width of the captured image to control the brightness of the captured image and appropriate image processing is performed on the captured image.

In FIG. 1, the graph in a solid line illustrates an input-output relationship in an SDR display device; the graph in a dashed dotted line illustrates an input-output relationship in an HDR display device with a large mask width (having large diameter of the insertion portion of the rigid endoscope (large diameter)); and the graph in a dashed two-dotted line illustrates an input-output relationship in an HDR display device with a small mask width (having smaller diameter of the insertion portion of the rigid endoscope (small diameter)). As illustrated in FIG. 1, the captured image according to the embodiment undergoes gamma correction and inverse gamma correction, and then will be output as a final medical photographic image.

For example, in a case where the display device that displays a medical photographic image is an HDR display device and the rigid endoscope has a small diameter, the control of a first parameter (digital gain or the like) described below is performed such that the observation target is to be imaged with lower brightness than SDR but higher brightness than a case where the rigid endoscope has a large diameter. As a result, as illustrated in the graph (left side) of the captured image at the time of imaging in FIG. 1, the output of the HDR display device is smaller than the output of the SDR display device, and is greater than the case where the rigid endoscope has a large diameter. Furthermore, in a case where the display device that displays a medical photographic image is an HDR display device and the rigid endoscope has a small diameter, for example, the control of a second parameter (exposure time and the like) described below is performed such that the observation target is to be imaged with lower brightness than SDR but the same brightness as a case where the rigid endoscope has a large diameter. As a result, as illustrated in the graph (right side) of the captured image at the time of imaging in FIG. 1, the output of the HDR display device is smaller than the output of the SDR display device, and is the same as the case where the rigid endoscope has a large diameter. Furthermore, by performing gamma correction and inverse gamma correction on the captured image in the case of the HDR display device, the HDR display device may achieve larger output than the output by the SDR display device as illustrated in the graph of the corrected captured image in FIG. 1.

Furthermore, the captured image is subjected to image processing according to the diameter of the rigid endoscope. Specifically, parameters used for image processing such as gain adjustment and noise reduction are calculated in accordance with the diameter of the rigid endoscope, whereby image processing suitable for the rigid endoscope is performed.

Hereinabove, the outline of the embodiment has been described with reference to FIG. 1. Next, the embodiments will be described.

Figure 2:
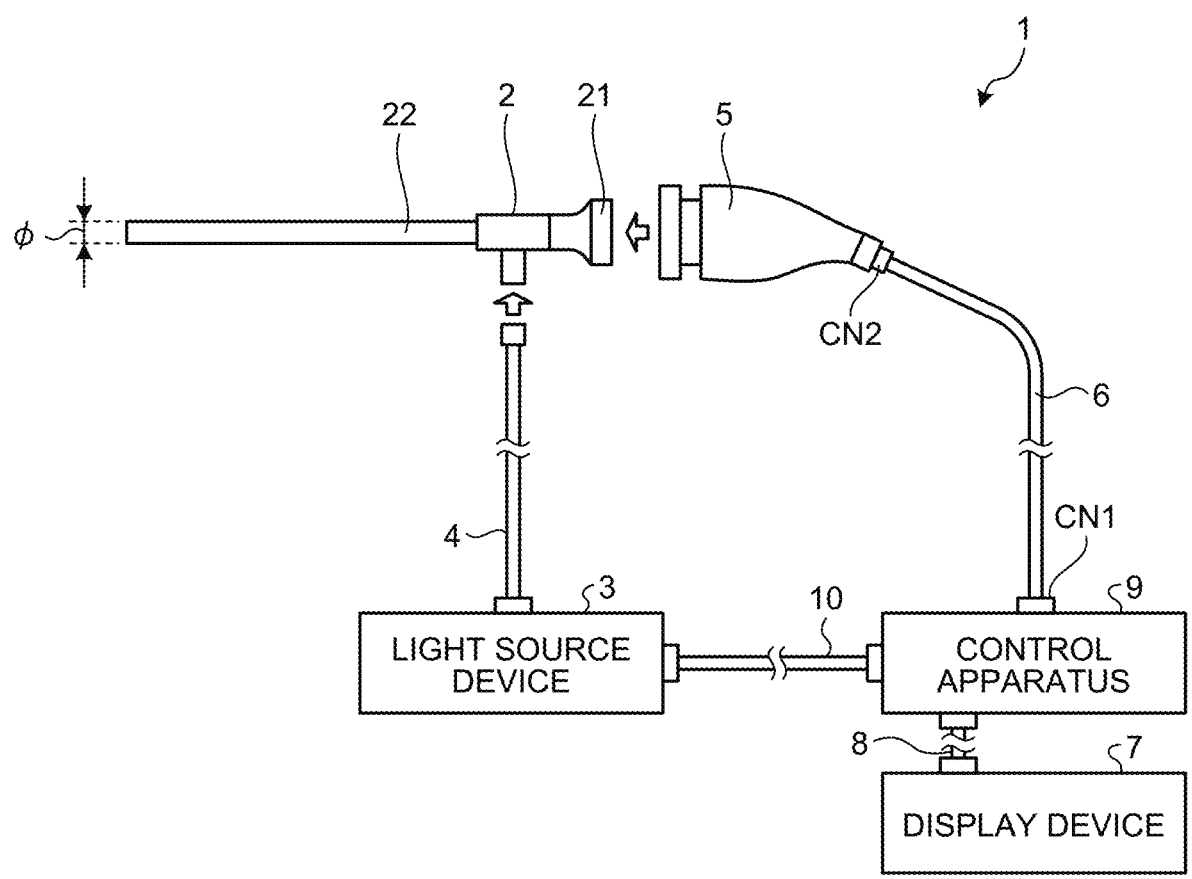
FIG. 2 is a schematic view illustrating a configuration of an entire endoscope apparatus including a medical control apparatus according to the embodiment.

Schematic configuration of endoscope apparatus FIG. 2 is a schematic view illustrating a configuration of an entire endoscope apparatus including a medical control apparatus according to the embodiment. An endoscope apparatus 1 is an apparatus used in the medical field for observing internal portions of a living organism. As illustrated in FIG. 2, the endoscope apparatus 1 includes a rigid endoscope 2, a light source device 3, a light guide 4, a camera head 5, a first transmission cable 6, a display device 7, a second transmission cable 8, a control apparatus 9, and a third transmission cable 10.

The rigid endoscope 2 is detachably connected to the camera head 5. As illustrated in FIG. 2, the rigid endoscope 2 includes an eyepiece 21 and an insertion portion 22.

The eyepiece 21 is connected with the camera head 5. The insertion portion 22 is either rigid or at least partially flexible and has an elongated shape, and is inserted into the living organism. The rigid endoscope 2 includes an optical system using one or a plurality of lenses to perform focusing of a subject image. The diameter ϕ of the insertion portion 22 has a variation of 2.7 mm, 4 mm, 5 mm, or 10 mm, for example, and the rigid endoscope 2 to be connected to the camera head 5 may be selected appropriately for the purpose of endoscopic observation. The larger the diameter ϕ of the insertion portion 22, the larger the amount of light introduced by the rigid endoscope, leading to the larger mask width described below.

The light source device 3 is connected to one end of the light guide 4, and supplies light for illuminating the inside of the living organism to the one end of the light guide 4 under the control of the control apparatus 9.

The light guide 4 has one end detachably connected to the light source device 3 and the other end detachably connected to the rigid endoscope 2. The light guide 4 transmits the light supplied from the light source device 3 from one end to the other end of the light guide 4 and supplies the light to the rigid endoscope 2. The light supplied to the rigid endoscope 2 is emitted from a distal end of the rigid endoscope 2 and applied to internal portions of the living organism. The light (subject image) applied to the internal portions of the living organism is collected and focused by the optical system in the rigid endoscope 2.

The camera head 5 is detachably connected to a proximal end (eyepiece 21 (FIG. 2)) of the rigid endoscope 2. Under the control of the control apparatus 9, the camera head 5 performs imaging, that is, captures a subject image introduced by the rigid endoscope 2, and outputs a captured image (RAW image) obtained by the imaging. The captured image is an image signal of 4K resolution or more.

A detailed configuration of the camera head 5 will be described below.

The first transmission cable 6 has one end detachably connected to the control apparatus 9 via a connector CN1 (FIG. 2), and has the other end detachably connected to the camera head 5 via a connector CN2 (FIG. 2). The first transmission cable 6 transmits the image signal or the like output from the camera head 5 to the control apparatus 9, and transmits a control signal, a synchronization signal, a clock, power, or the like output from the control apparatus 9 to the camera head 5 individually. Note that the image signal or the like transmitted from the camera head 5 to the control apparatus 9 via the first transmission cable 6 may be transmitted in an optical signal or in an electrical signal. The same applies to transmission of the control signal, the synchronization signal, and the clock from the control apparatus 9 to the camera head 5 via the first transmission cable 6.

The display device 7 is implemented by a display using liquid crystal, organic electroluminescence (EL), or the like, and displays an image based on a medical photographic image from the control apparatus 9 under the control of the control apparatus 9. The detailed configuration of the display device 7 will be described below.

The second transmission cable 8 has one end detachably connected to the display device 7 and the other end detachably connected to the control apparatus 9. The second transmission cable 8 transmits the medical photographic image processed by the control apparatus 9 to the display device 7.

The control apparatus 9 includes a central processing unit (CPU), or the like, and comprehensively controls operation of the light source device 3, the camera head 5, and the display device 7. Furthermore, the control apparatus 9 performs image processing on the captured image to generate a medical photographic image to be displayed on the display device 7. The detailed configuration of the control apparatus 9 will be described below.

The third transmission cable 10 has one end detachably connected to the light source device 3 and the other end detachably connected to the control apparatus 9. The third transmission cable 10 transmits the control signal from the control apparatus 9 to the light source device 3.

Figure 3:
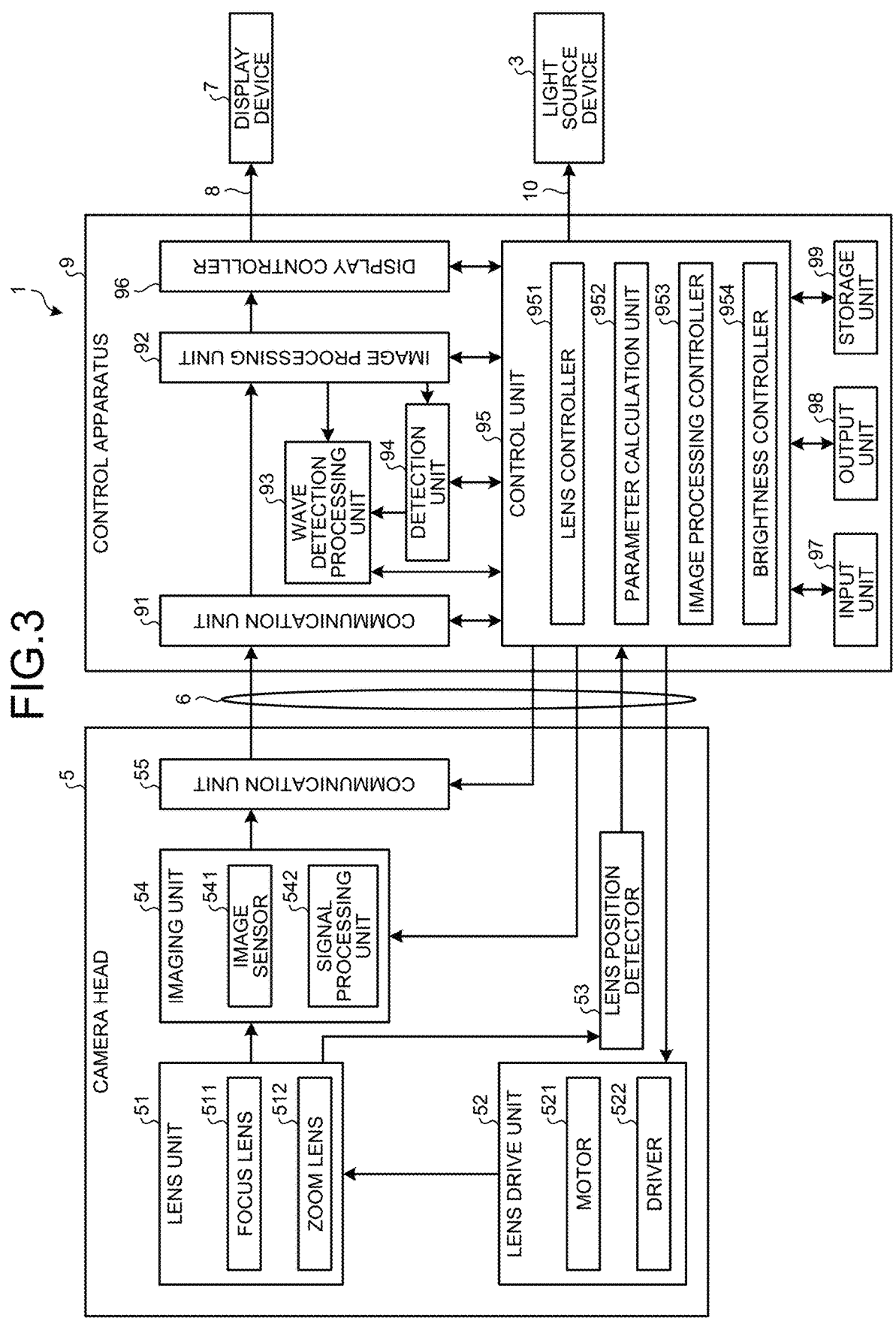
FIG. 3 is a block diagram illustrating a configuration of a camera head and a control apparatus.

Configuration of camera head Next, a configuration of the camera head 5 will be described. FIG. 3 is a block diagram illustrating a configuration of the camera head 5 and the control apparatus 9. For convenience of explanation, FIG. 3 omits illustration of connectors CN1 and CN2 between the control apparatus 9/the camera head 5 and the first transmission cable 6, and connectors between the control apparatus 9/the display device 7 and the second transmission cable 8, and connectors between the control apparatus 9/the light source device 3 and the third transmission cable 10.

As illustrated in FIG. 2, the camera head 5 includes a lens unit 51, a lens drive unit 52, a lens position detector 53, an imaging unit 54, and a communication unit 55.

The lens unit 51 is constituted with a plurality of lenses movable along the optical axis, and brings the subject image introduced by the rigid endoscope 2 into focus on an imaging surface of the imaging unit 54 (image sensor 541 (FIG. 3)). As illustrated in FIG. 3, the lens unit 51 includes a focus lens 511 and a zoom lens 512.

The focus lens 511 is constituted with one or more lenses and adjusts the focus by moving along the optical axis.

The zoom lens 512 is constituted with one or more lenses, and adjusts the angle of view by moving along the optical axis. Furthermore, the lens unit 51 includes a focus mechanism (not illustrated) that moves the focus lens 511 along the optical axis and an optical zoom mechanism (not illustrated) that moves the zoom lens 512 along the optical axis.

As illustrated in FIG. 3, the lens drive unit 52 includes: a motor 521 that operates the focus mechanism and the optical zoom mechanism described above; and a driver 522 that drives the motor 521. The lens drive unit 52 drives the lens unit 51 to adjust the focal point and the angle of view of the lens unit 51 under the control of the control apparatus 9.

The lens position detector 53 is constituted with a position sensor such as a photo interrupter, and configured to detect the lens position of the focus lens 511 (hereinafter referred to as the focus position) and the lens position of the zoom lens 512 (hereinafter referred to as the zoom position). Subsequently, the lens position detector 53 outputs a detection signal according to the focus position and the zoom position to the control apparatus 9 via the first transmission cable 6.

The imaging unit 54 images the inside of the living organism under the control of the control apparatus 9. As illustrated in FIG. 2, the imaging unit 54 includes the image sensor 541 and a signal processing unit 542.

The image sensor 541 is implemented by a charge coupled device (CCD), a complementary metal oxide semiconductor (CMOS), or the like that receives the subject image that has been introduced by the rigid endoscope 2 and focused by the lens unit 51 and converts the subject image into an electrical signal (analog signal).

The signal processing unit 542 performs signal processing on the electrical signal (analog signal) from the image sensor 541 and outputs a captured image (RAW image (digital signal)). For example, the signal processing unit 542 performs signal processing such as processing of removing reset noise, processing of multiplying an analog gain to amplify the analog signal, A/D conversion, or the like on an electrical signal (analog signal) from the image sensor 541.

The communication unit 55 functions as a transmitter that transmits the image signal (RAW signal (digital signal)) output from the imaging unit 54 to the control apparatus 9 via the first transmission cable 6. For example, the communication unit 55 includes a high-speed serial interface that performs image signal communication with the control apparatus 9 via the first transmission cable 6 at a transmission rate of 1 Gbps or more.

Configuration of control apparatus Next, the configuration of the control apparatus 9 will be described with reference to FIG. 3. As illustrated in FIG. 3, the control apparatus 9 includes a communication unit 91, an image processing unit 92, a wave detection processing unit 93, a detection unit 94, a control unit 95, a display controller 96, an input unit 97, an output unit 98, and a storage unit 99.

The communication unit 91 functions as a receiver that receives the captured image (RAW image (digital signal)) output from the camera head 5 (communication unit 55) via the first transmission cable 6. For example, the communication unit 91 includes a high-speed serial interface that performs image signal communication with the communication unit 55 at a transmission rate of 1 Gbps or more.

Under the control of the control unit 95, the image processing unit 92 processes the captured image (RAW image (digital signal)) output from the camera head 5 (communication unit 55) and received by the communication unit 91. Specifically, the image processing unit 92 performs image processing on the captured image using the first parameter calculated by a parameter calculation unit 952. For example, the image processing unit 92 multiplies the captured image (RAW image (digital signal)) by a digital gain for the amplification of the digital signal. Furthermore, on the captured image (RAW image (digital signal)) that has undergone black level adjustment and multiplication of the digital gain, the image processing unit 92 performs RAW processing such as demosaic processing to convert the RAW image (captured image) to RGB signals (image signals). Furthermore, on the RGB signal (image signal), the image processing unit 92 performs RGB processing such as white balance adjustment process of multiplying gains individually to the RGB values, RGB gamma correction, and YC conversion (conversion of RGB signals to luminance signals and color difference signals (Y, $C_B/C_R$ signals)). Furthermore, the image processing unit 92 executes YC processing such as color difference correction, noise reduction, shading, and enhancement on the Y, $C_B/C_R$ signals (image signals).

The wave detection processing unit 93 inputs the image signals (Y, $C_B/C_R$ signals) processed by the image processing unit 92, and executes wave detection processing based on the image signals (Y, $C_B/C_R$ signals). For example, based on pixel information (luminance signal (Y signal)) for each of pixels in a predetermined area (hereinafter referred to as a wave detection area) in the entire captured image of one frame captured by the image sensor 541, the wave detection processing unit 93 executes detection of the contrast and frequency components of the image within the wave detection area, detection of the mean value of the luminance and the maximum/minimum luminance pixels in the wave detection area using a filter or the like, determination by comparison with a threshold, and detection of the histogram or the like. Subsequently, the wave detection processing unit 93 outputs the wave detection information (contrast, frequency component, a mean value of luminance, maximum/minimum luminance pixels, histogram, or the like) obtained by the detection to the control unit 95.

Figure 4:
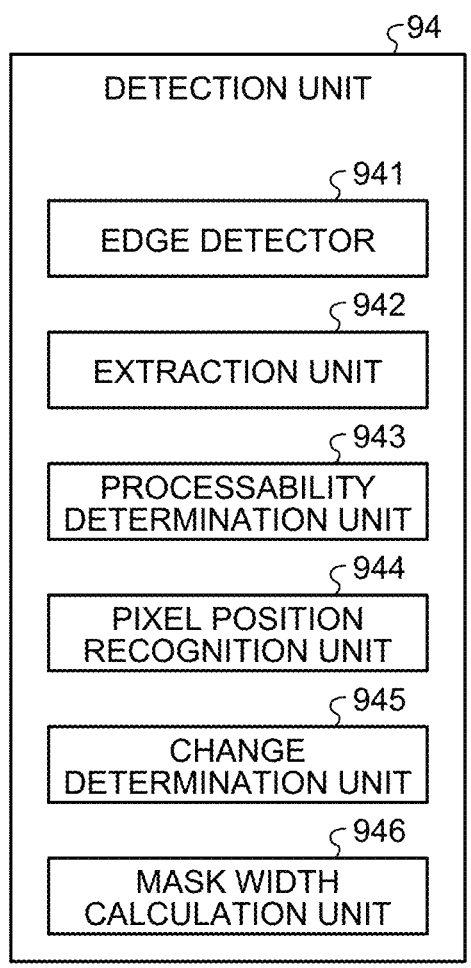
FIG. 4 is a block diagram illustrating a configuration of a detection unit.

FIG. 4 is a block diagram illustrating a configuration of the detection unit 94. The detection unit 94 performs a mask edge detection process and first and second determination processes based on the luminance signal (Y signal) contained in the image signals (Y, $C_B/C_R$ signals) processed by the image processing unit 92. As illustrated in FIG. 4, the detection unit 94 includes an edge detector 941, an extraction unit 942, a processability determination unit 943, a pixel position recognition unit 944, a change determination unit 945, and a mask width calculation unit 946.

The edge detector 941 executes a mask edge detection process described below based on a user operation of calculating a white balance gain (gain used in the white balance adjustment process performed by the image processing unit 92) to the input unit 97 (hereinafter referred to as a white balance setting operation) and based on a determination result of the first determination process performed by the processability determination unit 943.

FIG. 5 is a diagram illustrating a process of detecting the mask width. Specifically, (a) of FIG. 5 is a diagram illustrating an example of a captured image CI1 captured by an image sensor. (b) of FIG. 5 is a diagram illustrating the distribution of luminance values on a horizontal line L7 in the captured image CI1 illustrated in (a) of FIG. 5.

Here, the light (subject image) reflected in the living organism and introduced into the rigid endoscope 2 has a substantially circular cross section. Accordingly a subject image SI1 in the captured image CI1 has a substantially circular shape as illustrated in (a) of FIG. 5. That is, the captured image CI1 includes the subject image SI1 and a mask area MA1 (filled portion in (a) of FIG. 5) being areas other than the subject image SI1. By executing the mask edge detection process, the edge detector 941 detects a boundary point BP ((a) of FIG. 5) between the subject image SI1 and the mask area MA1.

Specifically, as illustrated in (a) of FIG. 5, the edge detector 941 acquires the luminance signal (Y signal) from among the image signals (Y, $C_B/C_R$ signals) processed by the image processing unit 92. Subsequently, the edge detector 941 detects the distribution of the luminance values of a plurality of (14 in the embodiment) horizontal lines L1 to L14 in the captured image CI1 based on the luminance signal (Y signal). Here, in the captured image CI1, the luminance value is higher in the area of the subject image SI1 than in the mask area MA1. That is, for example, as illustrated in (b) of FIG. 5, the luminance distribution on the horizontal line L7 indicates a high luminance value between the two boundary points BP dividing the subject image SI1 and the mask area MA1, and a low luminance value in the other portions. Based on this, the edge detector 941 compares the luminance value with a first luminance threshold SB11 ((b) of FIG. 5) and then determines an area in which pixels having a luminance value higher than the first luminance threshold SB11 are continuously arranged, as the subject image SI1.

Furthermore, the edge detector 941 compares the luminance value with a second luminance threshold SB12 ((b) of FIG. 5) lower than the first luminance threshold SB11 and then determines an area in which pixels having a luminance value lower than the second luminance threshold SB12 are continuously arranged, as the mask area MA1. Subsequently, the edge detector 941 recognizes the boundary point BP ((a) of FIG. 5) dividing the subject image SI1 and the mask area MA1. Furthermore, by executing the above process for all the horizontal lines L1 to L14, the edge detector 941 recognizes a plurality of boundary point BPs dividing the subject image SI1 and the mask area MA1.

The extraction unit 942 acquires the luminance signal (Y signal) from among the image signals (Y, $C_B/C_R$ signals) processed by the image processing unit 92. Subsequently, based on the luminance signal (Y signal), the extraction unit 942 compares the luminance value of each of the pixels on the horizontal line L7 ((a) of FIG. 5) located at the center in the captured image CI1 with the first luminance threshold SB11, and extracts a first pixel having a luminance value higher than the first luminance threshold SB11. Furthermore, the extraction unit 942 compares the luminance value on the horizontal line L7 with the second luminance threshold SB12, and extracts a second pixel having a luminance value higher than the second luminance threshold SB12.

The processability determination unit 943 executes the first determination process illustrated below. That is, the processability determination unit 943 compares the number of pixels constituted by the first pixels extracted by the extraction unit 942 being continuously arranged on the horizontal line L7 (hereinafter referred to as a first continuous pixel number N1 (refer to FIG. 14)) with a first pixel number threshold SN1 (refer to (a) of FIG. 14), and determines whether the state is a processable state where the first continuous pixel number N1 is the first pixel number threshold SN1 or more, or the state is an unprocessable state where the first continuous pixel number N1 is less than the first pixel number threshold SN1.

Furthermore, the processability determination unit 943 compares the number of pixels constituted by the second pixels extracted by the extraction unit 942 being continuously arranged on the horizontal line L7 (hereinafter referred to as a second continuous pixel number N2 (refer to FIG. 14)) with a second pixel number threshold SN2 (refer to (a) of FIG. 14), and determines whether the state is a processable state where the second continuous pixel number N2 is the second pixel number threshold SN2 or more, or the state is an unprocessable state where the second continuous pixel number N2 is less than the second pixel number threshold SN2. Then, the processability determination unit 943 outputs a detection signal corresponding to the determination result of the first determination process to the control unit 95.

In a case where the processability determination unit 943 determines that the state is the processable state, the pixel position recognition unit 944 recognizes the pixel position of the second pixel in which the second continuous pixel number N2 is the second pixel number threshold SN2 or more.

The change determination unit 945 executes the second determination process described below. That is, the change determination unit 945 determines whether all the pixels at the pixel position recognized by the pixel position recognition unit 944 have been extracted as the second pixels by the extraction unit 942 after the mask edge detection process performed by the edge detector 941.

The mask width calculation unit 946 calculates a mask width MW1 ((b) of FIG. 5) based on the position information of the boundary point BP. Specifically, the mask width calculation unit 946 calculates a distance between the two boundary points BP located on the horizontal line L7 located in the center of the captured image CI1, as the mask width MW1. The mask width MW1 corresponds to the amount of light introduced by the rigid endoscope 2, and thus, the larger the mask width MW1, the larger the amount of light introduced by the rigid endoscope 2. The amount of light introduced by the rigid endoscope 2 is determined by the diameter of the insertion portion 22, the optical system, or the like, and the larger the diameter of the insertion portion 22, the larger the amount of light introduced by the rigid endoscope 2.

The control unit 95 is implemented by using a CPU, for example, and outputs a control signal via the first to third transmission cables 6, 8 and 10, thereby controlling operations of the light source device 3, the camera head 5, and the display device 7, as well as controlling entire operation of the control apparatus 9.

As illustrated in FIG. 3, the control unit 95 includes a lens controller 951, a parameter calculation unit 952, an image processing controller 953, and a brightness controller 954.

The lens controller 951 controls the lens drive unit 52 to operate so as to adjust the focus and angle of view of the lens unit 51 (change the focus position and zoom position). For example, the lens controller 951 calculates an in-focus evaluation value for evaluating an in-focus state of the subject image SI1 included in the captured image CI1 based on the wave detection information (contrast and frequency components) output from the wave detection processing unit 93. Here, the lens controller 951 uses the contrast detected by the wave detection processing unit 93 and a sum of the high frequency components among the frequency components detected by the wave detection processing unit 93 to define the in-focus evaluation value. The in-focus evaluation value indicates that the larger the value, the higher focus is achieved. Subsequently, based on the focus position detected by the lens position detector 53 and the in-focus evaluation value, the lens controller 951 executes AF processing of positioning the focus lens 511 to the focus position at which the subject image SI1 is in focus by a hill climbing technique or the like. Note that the AF processing may employ a mode referred to as continuous AF that is continuously executed, or a mode referred to as a single or one-shot AF that is executed in response to an operation on an operation button (not illustrated) provided on the camera head 5 or the like.

The parameter calculation unit 952 calculates a first parameter used for image processing and a second parameter used for controlling the brightness of the captured image CI1 based on the mask width MW1 and the dynamic range of the display device 7. In the embodiment, the parameter calculation unit 952 calculates the first parameter related to image processing such as digital gain, noise reduction, shading, black level adjustment set value, and enhancement in the image processing unit 92. Furthermore, the parameter calculation unit 952 calculates the second parameter related to the brightness of the captured image CI1, such as the analog gain in the signal processing of the imaging unit 54, the exposure time of each of pixels of the image sensor 541 of the imaging unit 54, and the amount of light supplied from the light source device 3 to the insertion portion 22. Furthermore, the parameter calculation unit 952 calculates the gain to be multiplied by each of the RGB values in the white balance adjustment process performed by the image processing unit 92. Subsequently, the parameter calculation unit 952 outputs a control signal to the image processing unit 92, and sets the gain obtained by multiplying the RGB values by the white balance adjustment process performed by the image processing unit 92, as the calculated gain.

The image processing controller 953 controls the operation of the image processing unit 92 based on the first parameter calculated by the parameter calculation unit 952. Specifically, the image processing controller 953 outputs a control signal to the image processing unit 92 so as to control various types of image processing performed by the image processing unit 92 by using the first parameter calculated by the parameter calculation unit 952. With the control of the operation of the image processing unit 92 by the image processing controller 953, the captured image CI1 will undergo appropriate image processing corresponding to the mask width MW1 and the dynamic range of the display device 7.

The brightness controller 954 controls the operations of the image sensor 541, the signal processing unit 542, and the light source device 3 based on the second parameter calculated by the parameter calculation unit 952.

Specifically, the brightness controller 954 outputs a control signal to the imaging unit 54 via the first transmission cable 6 so as to control the exposure time of each of the pixels of the image sensor 541 by using the second parameter calculated by the parameter calculation unit 952. Furthermore, the brightness controller 954 outputs a control signal to the imaging unit 54 via the first transmission cable 6 so as to control the analog gain to be multiplied by the signal processing unit 542 using the second parameter calculated by the parameter calculation unit 952. In addition, the brightness controller 954 outputs a control signal to the light source device 3 via the third transmission cable 10 so as to control the amount of light to be supplied from the light source device 3 to the rigid endoscope 2 by using the second parameter calculated by the parameter calculation unit 952. With the control of the operations of the image sensor 541, the signal processing unit 542, and the light source device 3 by the brightness controller 954 as described above, the brightness of the captured image CI1 may be set to an appropriate brightness corresponding to the diameter of the insertion portion 22 and dynamic range of the display device 7.

The display controller 96 controls the display of the medical photographic image on the display device 7.

Regarding the control of the display of the medical photographic image, for example, the display controller 96 performs the display control process to control the brightness at the time of displaying the medical photographic image on the display device 7.

Here, gamma correction will be described with reference to FIG. 6. FIG. 6 is a diagram illustrating an example of an input-output relationship in a medical control apparatus. The horizontal axis of the graph illustrated in FIG. 6 illustrates the data input to the control apparatus 9, and the vertical axis illustrates the data output from the control apparatus 9.

Normally, it is ideal that the image corresponding to the input captured image be output to the display device 7 with no change of the image. In order for the image to be output as ideal, the gamma value indicating the input-output relationship in the display device 7 needs to be set to 1.0. However, the gamma value is typically set to 2.2 instead of 1.0 on the display device 7, due to execution of the processing of inverse gamma correction that decreases the RGB values of the input captured image to darken the medical photographic image corresponding to the captured image. Therefore, inputting the captured image in the unchanged state from the time of imaging to the display device 7 would result in the darker display of the medical photographic image due to the inverse gamma correction on the display device 7. To handle this, by preliminarily increasing the RGB value before the captured image is input to the display device 7, it is possible to prevent the medical photographic image from being displayed as a darker image on the display device 7. As described above, the process of increasing the RGB value in advance is referred to as gamma correction.

The input-output relationship when the gamma value is 1.0 is as illustrated by the broken line illustrated in FIG. 6. The input-output relationship when the gamma value is 2.2 is as illustrated by the solid line illustrated in FIG. 6, and the relationship corresponds to the input-output relationship on the SDR display device 7. The input-output relationship in the HDR display device 7 when the mask width is large (the diameter of the insertion portion 22 is large) is as illustrated in the dashed dotted line illustrated in FIG. 6. Furthermore, the input-output relationship in the HDR display device 7 when the mask width is small (the diameter of the insertion portion 22 is small) is as illustrated in the dashed two-dotted line illustrated in FIG. 6. The dashed dotted line and dashed two-dotted line indicate input-output relationships based on the hybrid log gamma (HLG) method. Note that the input-output relationship in the HDR display device 7 may be an input-output relationship based on the perceptual quantization (PQ) method.

In the control apparatus 9, the display controller 96 performs gamma correction on the captured image based on the gamma value of the display device 7, and displays a medical photographic image generated from the gamma-corrected captured image on the display device 7. For example, the display controller 96 performs gamma correction on the captured image so that an intermediate luminance values in the medical photographic image to be displayed on the display device 7 and another display device 7 having a predetermined gamma value will be the same. Specifically, the display controller 96 performs gamma correction such that when the medical photographic image is displayed on the HDR display device 7, the medical photographic image displayed on the HDR display device 7 and the medical photographic image displayed on an SDR display device 7 having a gamma value of 2.2 will have the same intermediate luminance value. With this process, the display device 7 may display the medical photographic image on the individual display devices 7, namely, the HDR display device 7 and the SDR display device 7 so as to achieve the same visibility for the medical photographic image on both devices.

Furthermore, using on-screen display (OSD) processing or the like, under the control of the control unit 95, the display controller 96 generates a medical photographic image for display obtained by superimposing an image (corresponding to alert information) including a message such as "Please perform white balance setting operation again" on the captured image CI1 based on the image signals (Y, $C_B/C_R$ signals) processed by the image processing unit 92. The display controller 96 then outputs the medical photographic image to the display device 7 via the second transmission cable 8.

The input unit 97 is constituted with an operation device such as a mouse, a keyboard, and a touch panel, and receives user operation (for example, white balance setting operation) performed by a user such as a doctor.

Subsequently, the input unit 97 outputs an operation signal corresponding to the user operation to the control unit 95.

The output unit 98 is constituted with a speaker, a printer, or the like, and outputs various types of information.

The storage unit 99 stores a program executed by the control unit 95, information needed for processing performed by the control unit 95, or the like.

Configuration of display device Hereinafter, an example of the functional configuration of the display device 7 will be described with reference to FIGS. 7 and 8. FIG. 7 is a diagram illustrating an example of an input-output relationship in a display device. In the graph illustrated in FIG. 7, the horizontal axis indicates data input to the display device 7, and the vertical axis indicates the data output from the display device 7.

The display device 7 includes at least a control unit (not illustrated). The control unit performs inverse gamma correction on the captured image in which RGB values have been increased in advance by gamma correction. With this process, the control unit decreases the RGB values of the captured image to bring it closer to the ideal input-output relationship illustrated in the broken line in FIG. 7, and then displays the captured image as a medical photographic image on the display device 7.

In a case where the medical photographic image is displayed on the SDR display device 7, the control unit performs inverse gamma correction based on the input-output relationship illustrated in the solid line in FIG. 7. The input-output relationship illustrated in the solid line illustrates the input-output relationship when the gamma value is 2.2. Furthermore, in a case where the medical photographic image is displayed on the captured image of HDR when the mask width is large (the diameter of the insertion portion 22 is large), the control unit performs inverse gamma correction based on the input-output relationship illustrated in the dashed dotted line illustrated in FIG. 7. Furthermore, in a case where the medical photographic image is displayed on the captured image of HDR when the mask width is small (the diameter of the insertion portion 22 is small), the control unit performs inverse gamma correction based on the input-output relationship illustrated by the dashed two-dotted line illustrated in FIG. 7. The input-output relationship illustrated by the dashed dotted line and the dashed two-dotted line each indicate the input-output relationships based on the HLG method. Note that the input-output relationship in the HDR display device 7 may be an input-output relationship based on the PQ method.

Figure 8:
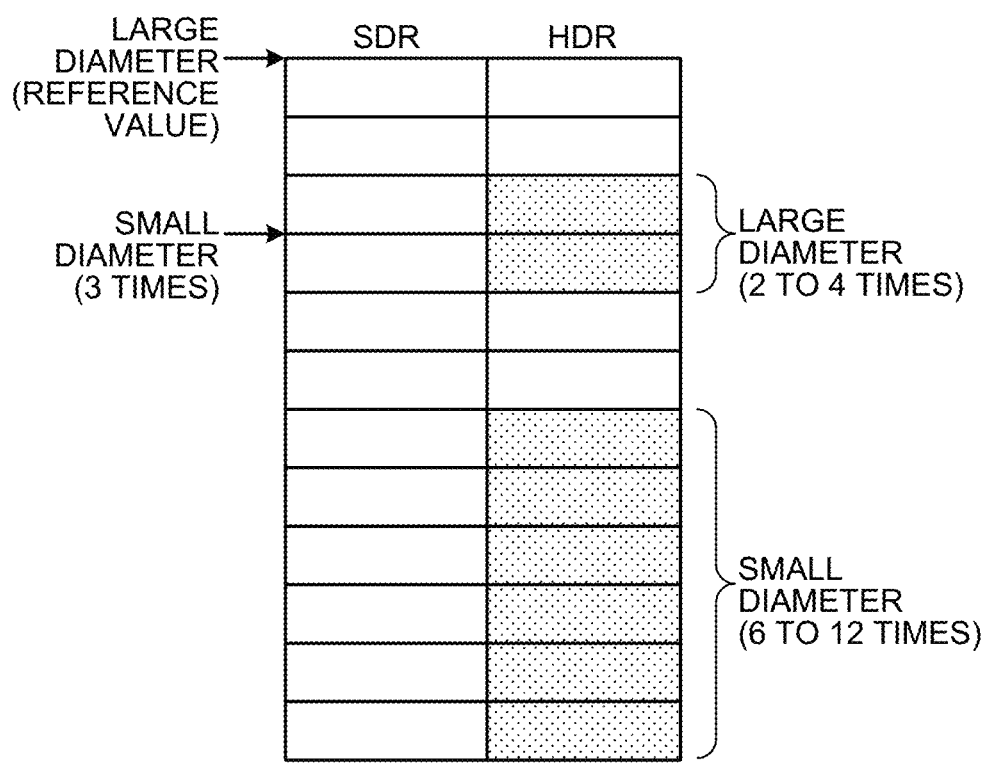
FIG. 8 is a diagram illustrating brightness of a medical photographic image.

FIG. 8 is a diagram illustrating brightness of a medical photographic image. FIG. 8 illustrates the brightness of the image under individual conditions using the medical photographic image displayed on the SDR display device 7 as a reference value. First, in a case where the mask width is small (the diameter of the insertion portion 22 is small), the amount of light introduced into the rigid endoscope 2 is smaller than the case where the mask width is large (the diameter of the insertion portion 22 is large). Accordingly, imaging is performed with the brightness lower than the brightness (for example, threefold difference, depending on the diameter of the insertion portion 22) in the case where the mask width is large (the diameter of the insertion portion 22 is large). Furthermore, the medical photographic image displayed on the HDR display device 7 is captured with lower brightness compared to the medical photographic image displayed on the SDR display device 7 (for example, two to four times of difference) because it is displayed on the HDR display device 7. In this case, the medical photographic image having a small mask width (the diameter of the insertion portion 22 is small) and displayed on the HDR display device 7 is captured with a brightness 6 to 12 times lower than the above reference value.

Outline of Processes in the Control Unit

The control unit 95 controls the operations of the image processing unit 92, the image sensor 541, the signal processing unit 542, and the light source device 3. Specifically, the control unit 95 specifies the dynamic range of the display device 7 based on the determination information. Next, the control unit 95 specifies the mask width MW1 based on the determination information. Subsequently, the control unit 95 determines the first parameter and the second parameter corresponding to the specified dynamic range and the mask width MW1 of the display device 7. More specifically, the control unit 95 performs a determination information acquisition process, a determination process, and a parameter determination process described below.

Determination Information Acquisition Process

The control unit 95 first acquires determination information. The determination information includes information for determining the display device 7 connected to the control apparatus 9 and information for determining the rigid endoscope 2 connected to the camera head 5, and may include operation information, dynamic range information, and mask width information.

The operation information is information related to an operation input by a predetermined operation performed by the user. For example, the user performs a selection operation of selecting the display device 7 on which a medical photographic image is to be displayed. The control unit 95 acquires information related to the display device 7 selected by the user as operation information (determination information).

The dynamic range information is information indicating the dynamic range of the display device 7. The control unit 95 acquires the dynamic range information from the display device 7 connected to the control apparatus 9, for example.

Furthermore, the control unit 95 may acquire identification information from the display device 7 connected to the control apparatus 9, and may acquire the dynamic range information regarding the display device 7 based on the acquired identification information. For example, the control unit 95 acquires the dynamic range information of the display device 7 by referring to the dynamic range information regarding the display device 7 registered in advance in the storage unit 99 of the control apparatus 9 based on the acquired identification information.

In the case where the control apparatus 9 and the display device 7 are connected by a cable or the like capable of only one-way communication, the control unit 95 may not acquire dynamic range information or identification information from the display device 7, and thus acquires the operation information described above. In contrast, in a case where the control apparatus 9 and the display device 7 are connected by a cable or the like capable of bidirectional communication, the control unit 95 acquires the dynamic range information or identification information described above from the display device 7. A cable capable of only one-way communication is, for example, a serial digital interface (SDI) cable or the like. The cable capable of bidirectional communication is, for example, a high-definition multimedia interface (HDMI) (registered trademark) cable, a Display Port cable, or the like. Note that, when the control apparatus 9 and the display device 7 are connected by an SDI cable, the control apparatus 9 may transmit a user ID to the display device 7, and the display device 7 may perform inverse gamma correction and brightness adjustment in accordance with the user ID. In this case, it is assumed that the user ID is associated with the display device 7 used by the user.

The mask width is the mask width MW1 of the captured image CI1 calculated by the mask width calculation unit 946 described above. The mask width MW1 is a diameter of a circle formed by the boundary point BP dividing the subject image SI1 and the mask area MA1 which is an area that may not be imaged because the light is physically shielded by a lens barrel of the insertion portion 22 when the insertion portion 22 captures the subject image. Accordingly, the size of the mask area MA1 differs depending on the diameter $\phi$ of the insertion portion 22 (refer to FIG. 2). The control unit 95 acquires information (determination information) representing the mask width MW1 from the detection unit 94. Alternatively, in a case where the control apparatus 9 does not have the detection unit 94, the control unit 95 may acquire the mask width based on the operation information regarding the rigid endoscope 2 selected by the user. Furthermore, the control unit 95 may acquire the mask width from the identification information acquired from the rigid endoscope 2. In this case, the storage unit 99 of the control apparatus 9 records a table indicating the correspondence between the identification information of the rigid endoscope 2 and the mask width.

Determination Process

The control unit 95 specifies the dynamic range of the display device 7 and the mask width MW1 based on the acquired determination information. For example, the control unit 95 specifies the dynamic range of the display device 7 based on a predetermined selection operation.

Specifically, the control unit 95 confirms the display device 7 selected by the selection operation performed by the user from the operation information acquired as the determination information. Then, the control unit 95 specifies the dynamic range of the display device 7 selected by the user as the dynamic range of the display device 7 connected to the control apparatus 9.

Furthermore, the control unit 95 specifies the dynamic range of the display device 7 based on the dynamic range information acquired as the determination information. Specifically, the control unit 95 specifies the dynamic range indicated by the dynamic range information acquired as the determination information, as the dynamic range of the display device 7 connected to the control apparatus 9. Furthermore, the control unit 95 confirms the mask width based on the mask width MW1 acquired as the determination information. Specifically, the control unit 95 specifies the mask area MA1 acquired as the determination information, as the mask width.

Based on the dynamic range of the display device 7 and the mask width MW1 specified in the determination process, the control unit 95 determines how the imaging unit 54 is to be controlled to perform imaging of the observation target and how the image processing is to be performed on the captured image. For example, when the dynamic range of the display device 7 is HDR, the display device 7 displays the medical photographic image with high luminance. Therefore, the control unit 95 determines to control the imaging unit 54 to perform imaging of the observation target with lowered brightness. In contrast, when the dynamic range of the display device 7 is SDR, the display device 7 displays the medical photographic image without increasing the luminance. Therefore, the control unit 95 determines to control the imaging unit 54 to perform imaging of the observation target without lowering brightness. For example, in a case where the mask width is small (the insertion portion 22 has a small diameter), imaging is performed with a lowered brightness compared to the case where the mask width is large (the insertion portion 22 has a large diameter), as described in FIG. 8. Therefore, the control unit 95 determines to control to decrease the gain in the image processing unit 92 to be lower than the gain in the case where the mask width is large (the insertion portion 22 has a large diameter).

Parameter Determination Process

The control unit 95 determines the first parameter and the second parameter in accordance with the result of the determination process. For example, when it is determined to control the imaging unit 54 to perform imaging of the observation target with a lowered brightness, the control unit 95 compares the dynamic range of the display device 7 with a predetermined dynamic range, and determines the second parameter based on the comparison result.

Specifically, the control unit 95 extracts a difference between the maximum value of the dynamic range of the display device 7 and the maximum value of the predetermined dynamic range, and determines the second parameter based on the difference.

For example, when the maximum value of the dynamic range of the display device 7 is n times (n is a real number) the maximum value of the predetermined dynamic range, the control unit 95 sets the brightness target value determined by the second parameter of the display device 7 to the value being 1/n times the brightness target value determined by the second parameter corresponding to the predetermined dynamic range. Specifically, there is an assumable case where the dynamic range of the display device 7 connected to the control apparatus 9 is HDR, and the maximum value of the dynamic range of the HDR display device 7 is twice the maximum dynamic range of the SDR display device 7. In this case, the control unit 95 sets the brightness target value determined by the second parameter of the HDR display device 7 to ½ of the brightness target value determined by the second parameter of the SDR display device 7.

The second parameter may be determined so as to increase the brightness for the time when the imaging unit 54 images the observation target. Furthermore, the magnification for multiplying the target value corresponding to the predetermined dynamic range in calculating the target value of brightness on the display device 7 is not limited to 1/n times, and may be set to an arbitrary magnification.

For example, when the control unit 95 determines to decrease the gain in the image processing unit 92, the control unit 95 compares the mask area MA1 of the captured image CI1 with a predetermined mask width, and determines the first parameter based on the comparison result.

Brightness Control Process

The control unit 95 controls the amount of light emitted by the light source device 3, for example, and thereby adjusts the brightness at the time when the imaging unit 54 images an observation target. Specifically, when it is desired to increase the brightness at the time of imaging, the control unit 95 increases the amount of light emitted by the light source device 3. This will increase the amount of light projected onto the observation target, leading to an increase in the brightness at the time of imaging, and to an increase in the brightness of the captured image as well. In contrast, when it is desired to decrease the brightness at the time of imaging, the control unit 95 decreases the amount of light emitted by the light source device 3. This will decrease the amount of light projected onto the observation target, leading to a decrease in the brightness at the time of imaging, and to a decrease in the brightness of the captured image as well.

Furthermore, the control unit 95 may control the exposure time of the image sensor 541 to adjust the brightness at the time when the imaging unit 54 performs imaging of the observation target, for example.

Specifically, when it is desired to increase the brightness at the time of imaging, the control unit 95 increases the exposure time of the image sensor 541. This will increase the amount of light received from the observation target, leading to an increase in the brightness at the time of imaging, and to an increase in the brightness of the captured image as well. In contrast, when it is desired to decrease the brightness at the time of imaging, the control unit 95 decreases the exposure time of the image sensor 541. This will decrease the amount of light received from the observation target, leading to a decrease in the brightness at the time of imaging, and to a decrease in the brightness of the captured image as well.

Furthermore, the control unit 95 may control the analog gain in the signal processing unit 542 to adjust the brightness of the captured image, for example.

Specifically, when it is desired to increase the brightness of the captured image, the control unit 95 increases the analog gain in the signal processing unit 542. This will increase the brightness of the captured image. In contrast, when it is desired to decrease the brightness of the captured image, the control unit 95 decreases the analog gain in the signal processing unit 542. This will decrease the brightness of the captured image.

Process of Controlling Image Processing

The control unit 95 controls the parameters used in the image processing performed by the image processing unit 92, such as digital gain, noise reduction, shading, black level adjustment set value, enhancement, for example, and thereby adjusts the image processing onto the captured image. Specifically, when the gain in the image processing unit 92 is increased (the insertion portion 22 has a small diameter), the noise contained in the captured image is also amplified, and therefore, the control unit 95 raises the noise reduction level in the image processing unit 92. This makes it possible to reduce the noise of the captured image. In contrast, when the gain is small (the insertion portion 22 has a large diameter), the control unit 95 lowers the noise reduction level in the image processing unit 92, and thereby reduces the level of deterioration in resolution and the blurring of the image due to noise reduction.

Similarly, when the gain in the image processing unit 92 is increased (the insertion portion 22 has a small diameter), unevenness in brightness in the captured image is also amplified, and therefore, the control unit 95 increases the shading level in the image processing unit 92. This makes it possible to reduce the unevenness in the brightness of the captured image. In contrast, when the gain is small (the insertion portion 22 has a large diameter), the control unit 95 lowers the shading level in the image processing unit 92, and thereby reduces the level of deterioration in resolution and the blurring of the image due to the shading. It is preferable that the control unit 95 achieves a match of the shading area with the subject image SI1 in accordance with the mask width MW1. This is because incorporating the mask area MA1 in the shading area would hinder execution of appropriate shading.

Similarly, when the gain in the image processing unit 92 is increased (the insertion portion 22 has a small diameter), the black level in the captured image is also raised, and therefore, the control unit 95 increases a set value of the black level adjustment in the image processing unit 92. In the black level adjustment, the portion darker (with lower luminance) than the set value is to be blacked out as the mask area MA1. This clarifies the boundary of the subject image SI1 and the mask area MA1. In contrast, when the gain is reduced (the insertion portion 22 has a large diameter), the control unit 95 decreases the set value of the black level adjustment in the image processing unit 92.

Similarly, when the gain in the image processing unit 92 is increased (the insertion portion 22 has a small diameter), the control unit 95 lowers the enhancement level in the image processing unit 92. This is because the noise becomes more noticeable with high level of enhancement. In contrast, when the gain is reduced (the insertion portion 22 has a large diameter), the control unit 95 increases the enhancement level in the image processing unit 92.

Other Control Processes

Furthermore, the control unit 95 may control one or more functions typically provided in an electronic imaging type microscope unit, such as control of an AF function, including a zoom function (optical zoom function and electronic zoom function), for example.

Operation of endoscope apparatus Hereinafter, an operation example of the endoscope apparatus 1 according to the embodiment will be described with reference to FIGS. 9 to 12.

(1) Operation Example of the Entire Endoscope Apparatus 1

Figure 9:
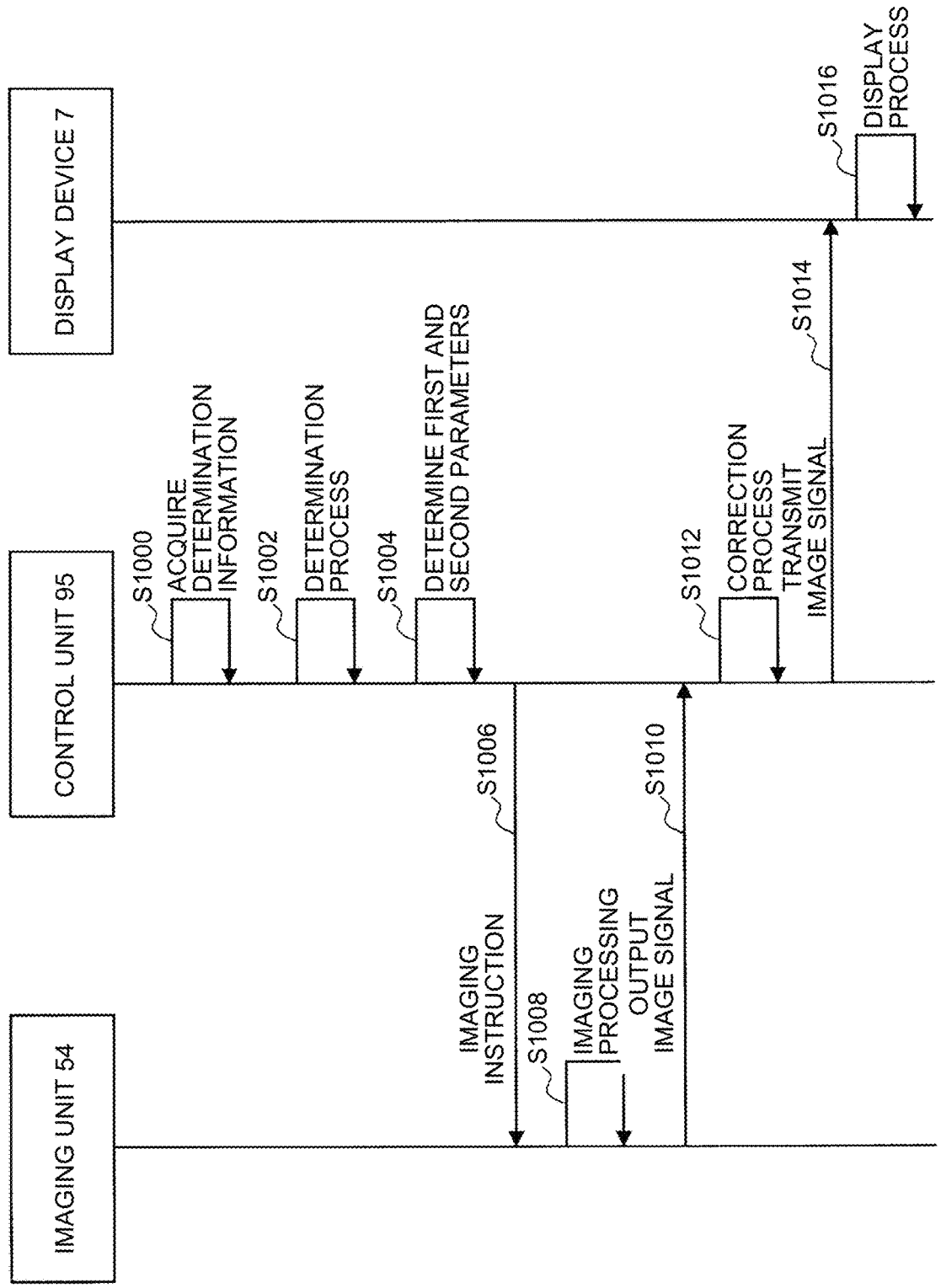
FIG. 9 is a sequence diagram illustrating a flow of operation of the medical control apparatus according to the embodiment.

First, an example of a series of operation up to the point where the endoscope apparatus 1 displays the medical photographic image on the display device 7 will be described. FIG. 9 is a sequence diagram illustrating a flow of operation of the medical control apparatus according to the embodiment.

As illustrated in FIG. 9, first, the control unit 95 acquires determination information (step S1000). Next, based on the acquired determination information, the control unit 95 performs a determination process of determining the dynamic range and the mask width MW1 of the display device 7 connected to the control apparatus 9 (step S1002). The detailed processing of the determination process will be described below. Next, the control unit 95 determines the first parameter and the second parameter based on the result of the determination process (step S1004). Subsequently, the control unit 95 outputs an imaging instruction to the imaging unit 54 so as to capture a medical photographic image corresponding to the determined second parameter (step S1006).

Having received the input of the imaging instruction from the control unit 95, the imaging unit 54 images the observation target in accordance with the imaging instruction (step S1008), and outputs the captured image obtained by the imaging to the control unit 95 (step S1010).

Having received an input of the captured image from the imaging unit 54, the control unit 95 performs a correction process on the captured image appropriate for the display device 7 to which the captured image is transmitted (step S1012). The detailed processing of the correction process will be described below. After the correction process, the control unit 95 transmits the corrected captured image to the display device 7 via the display controller 96 (step S1014).

Having received the captured image, the display device 7 performs a display process for displaying the captured image as a medical photographic image (step S1016). The detailed processing of the display process will be described below. After the medical photographic image is displayed on the display device 7 in the display process, the endoscope apparatus 1 ends the operation.

(2) Determination Process

Figure 10:
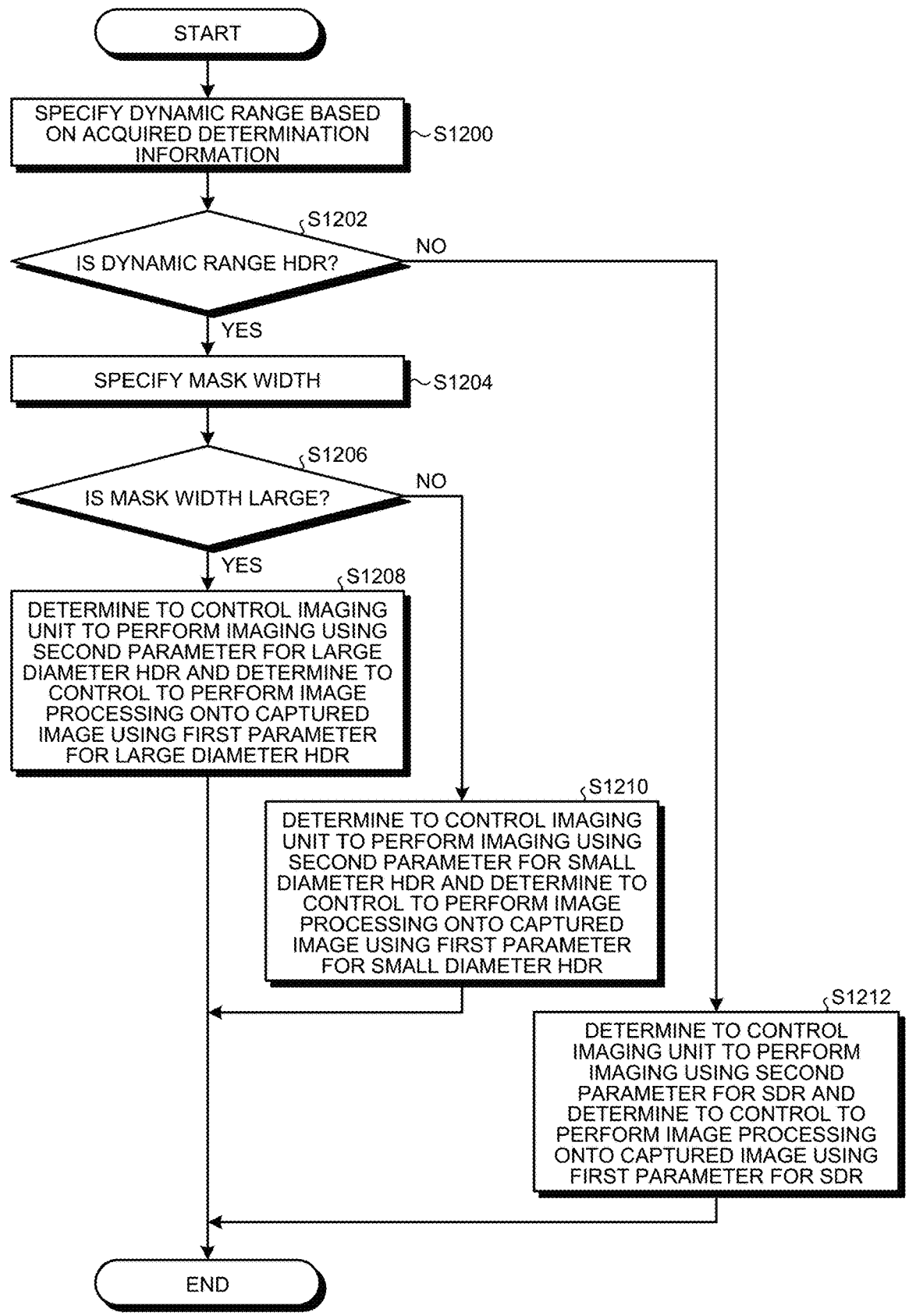
FIG. 10 is a flowchart illustrating a processing flow in a determination process according to the embodiment.

Next, detailed processing of the determination process in the control unit 95 according to the embodiment will be described. FIG. 10 is a flowchart illustrating a processing flow in a determination process according to the embodiment.

As illustrated in FIG. 10, first, the control unit 95 specifies the dynamic range of the display device 7 connected to the control apparatus 9 based on the acquired determination information (step S1200). Next, the control unit 95 confirms whether the specified dynamic range is HDR (step S1202). When the specified dynamic range is HDR (step S1202/YES), the control unit 95 specifies the mask width MW1 based on the acquired determination information (step S1204). The process of calculating the mask width MW1 will be described below. Next, the control unit 95 confirms whether the specified mask width MW1 is large (step S1206). When the specified mask width MW1 is larger than the predetermined value (step S1206/YES), the control unit 95 judges that the insertion portion 22 of the rigid endoscope 2 has a large diameter, and determines to control the imaging unit 54 to image the observation target using the second parameter for the large diameter HDR, and determines to control the image processing unit 92 to perform image processing onto the captured image using the first parameter for the large diameter HDR (step S1208).

In contrast, when the specified mask width MW1 is the predetermined value or less (step S1206/NO), the control unit 95 determines to control the imaging unit 54 to image the observation target using the second parameter for the small diameter HDR, and determines to control the image processing unit 92 to perform image processing onto the captured image using the first parameter for the small diameter HDR (step S1210). In addition, when the specified dynamic range is not HDR (step S1202/NO), the control unit 95 determines to control the imaging unit 54 to image the observation target using the second parameter for the SDR, and determines to control the image processing unit 92 to perform image processing onto the captured image using the first parameter for the SDR (step S1212: control step). The control unit 95 ends the determination process.

(3) Correction Process

Figure 11:
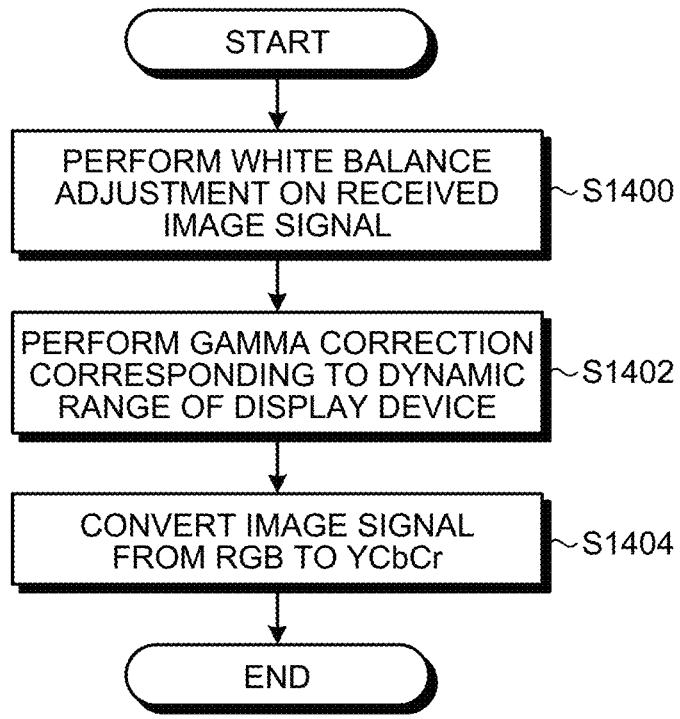
FIG. 11 is a flowchart illustrating a processing flow in a correction process according to the embodiment.

Next, detailed processing of the correction process in the control unit 95 according to the embodiment will be described. FIG. 11 is a flowchart illustrating a processing flow in the correction process according to the embodiment.

As illustrated in FIG. 11, first, the control unit 95 multiplies the input captured image by a digital gain, and thereafter performs RAW processing such as black level adjustment and demosaic processing on the image. Next, the control unit 95 converts the RAW image (captured image) into RGB signals (image signals) and performs white balance adjustment (step S1400). Next, the control unit 95 performs gamma correction in accordance with the dynamic range of the display device 7 and the diameter of the insertion portion 22 (step S1402). For example, when the dynamic range is HDR and the diameter of the insertion portion 22 is a large diameter, the control unit 95 performs gamma correction on the captured image using a gamma value for the large diameter HDR. When the dynamic range is HDR and the diameter of the insertion portion 22 is a small diameter, the control unit 95 performs gamma correction on the captured image using a gamma value for the small diameter HDR. When the dynamic range is SDR, the control unit 95 performs gamma correction on the captured image using a gamma value for SDR. Subsequently, the control unit 95 converts the gamma-corrected captured image from RGB to YCbCr (step S1404), and executes a YC processing such as color difference correction, noise reduction, shading, and enhancement on the Y, $C_B/C_R$ signals to complete the correction process. In the correction process, the first parameter is appropriately used for image processing such as digital gain, noise reduction, shading, black level adjustment set value, and enhancement.

(4) Display Process

Figure 12:
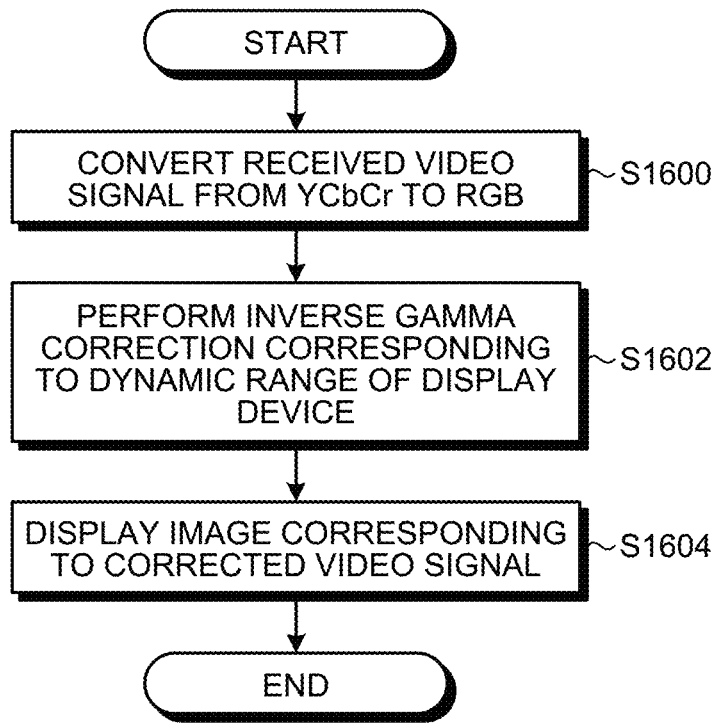
FIG. 12 is a flowchart illustrating a processing flow in a display process according to the embodiment.

Next, the detailed processing of the display process in the display device 7 according to the embodiment will be described. FIG. 12 is a flowchart illustrating a processing flow in the display process according to the embodiment.

As illustrated in FIG. 12, first, the display device 7 converts the received video signal from YCbCr to RGB (step S1600). Next, the display device 7 performs inverse gamma correction on the converted video signal in accordance with the dynamic range of the display device 7 and the diameter of the insertion portion 22 (step S1602). For example, when the dynamic range is HDR and the diameter of the insertion portion 22 is a large diameter, the display device 7 performs inverse gamma correction on the video signal using a gamma value for the large diameter HDR. For example, when the dynamic range is HDR and the diameter of the insertion portion 22 is a small diameter, the display device 7 performs inverse gamma correction on the video signal using a gamma value for the small diameter HDR. When the dynamic range is SDR, the display device 7 performs inverse gamma correction on the video signal using a gamma value for SDR. Subsequently, the display device 7 generates a medical photographic image corresponding to the corrected video signal, displays the generated medical photographic image (step S1604), and ends the display process.

Mask Width Calculating Process

Figure 13:
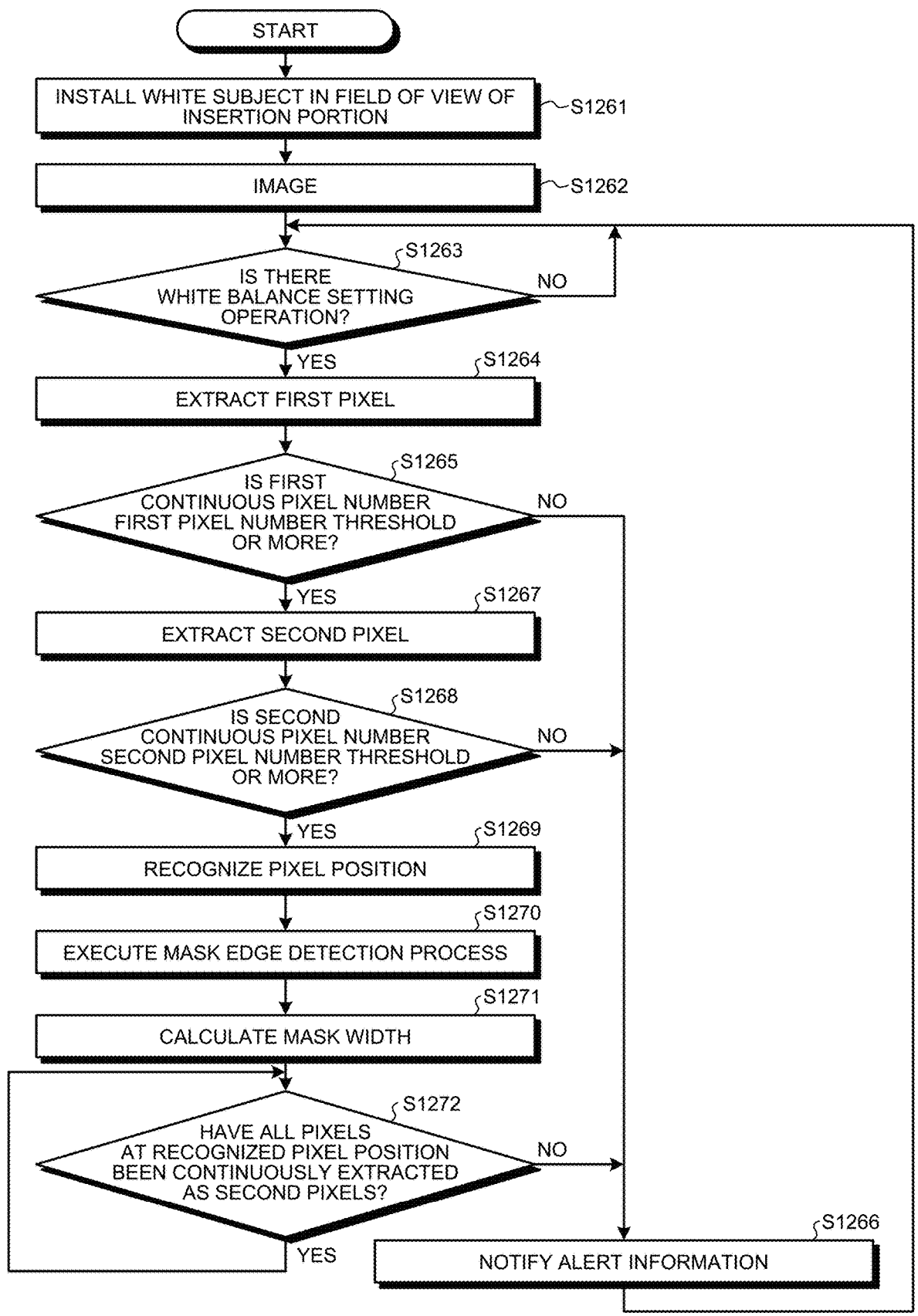
FIG. 13 is a flowchart illustrating the process of detecting the mask width.

Next, an operation (process of calculating the mask width) of the endoscope apparatus 1 described above will be described. FIG. 13 is a flowchart illustrating a process of detecting the mask width. FIG. 14 is a diagram illustrating operations of the endoscope apparatus. Specifically, FIG. 14 is a diagram illustrating the distribution of the luminance values on the horizontal line L7 located at the center in the captured image CI1 illustrated in (a) of FIG. 5. In the following, the operations of the detection unit 94, the wave detection processing unit 93, the display controller 96, and the display device 7 will be mainly described.

First, a user such as a doctor covers the distal end of the rigid endoscope 2 with a white subject such as gauze, and installs the subject in the field of view of the rigid endoscope 2 (step S1261: subject installation step).

Subsequently, the endoscope apparatus 1 starts imaging the subject (step S1262: imaging step).

After step S1262, the control unit 95 constantly monitors whether any white balance setting operation has been performed onto the input unit 97 (step S1263: operation reception step). That is, when it is judged that there is no white balance setting operation (step S1263: No), the monitoring in step S1263 is continued.

When it is judged that the white balance setting operation has been performed (step S1263: Yes), the extraction unit 942 acquires the luminance signal (Y signal) among the image signals (Y, $C_B/C_R$ signals) processed by the image processing unit 92. Subsequently, based on the luminance signal (Y signal), the extraction unit 942 compares the luminance value of each of the pixels on the horizontal line L7 located at the center in the captured image CI1 with the first luminance threshold SB11, and extracts a first pixel having a luminance value higher than the first luminance threshold SB11 (step S1264).

After step S1264, the processability determination unit 943 compares the first continuous pixel number N1 constituted by the first pixels extracted in step S1263 being continuously arranged on the horizontal line L7 with the first pixel number threshold SN1, and determines whether the first continuous pixel number N1 is the first pixel number threshold SN1 or more (whether the state is a processable state or an unprocessable state) (step S1265). Then, the processability determination unit 943 outputs a signal corresponding to the determination result to the control unit 95.

Figure 14:
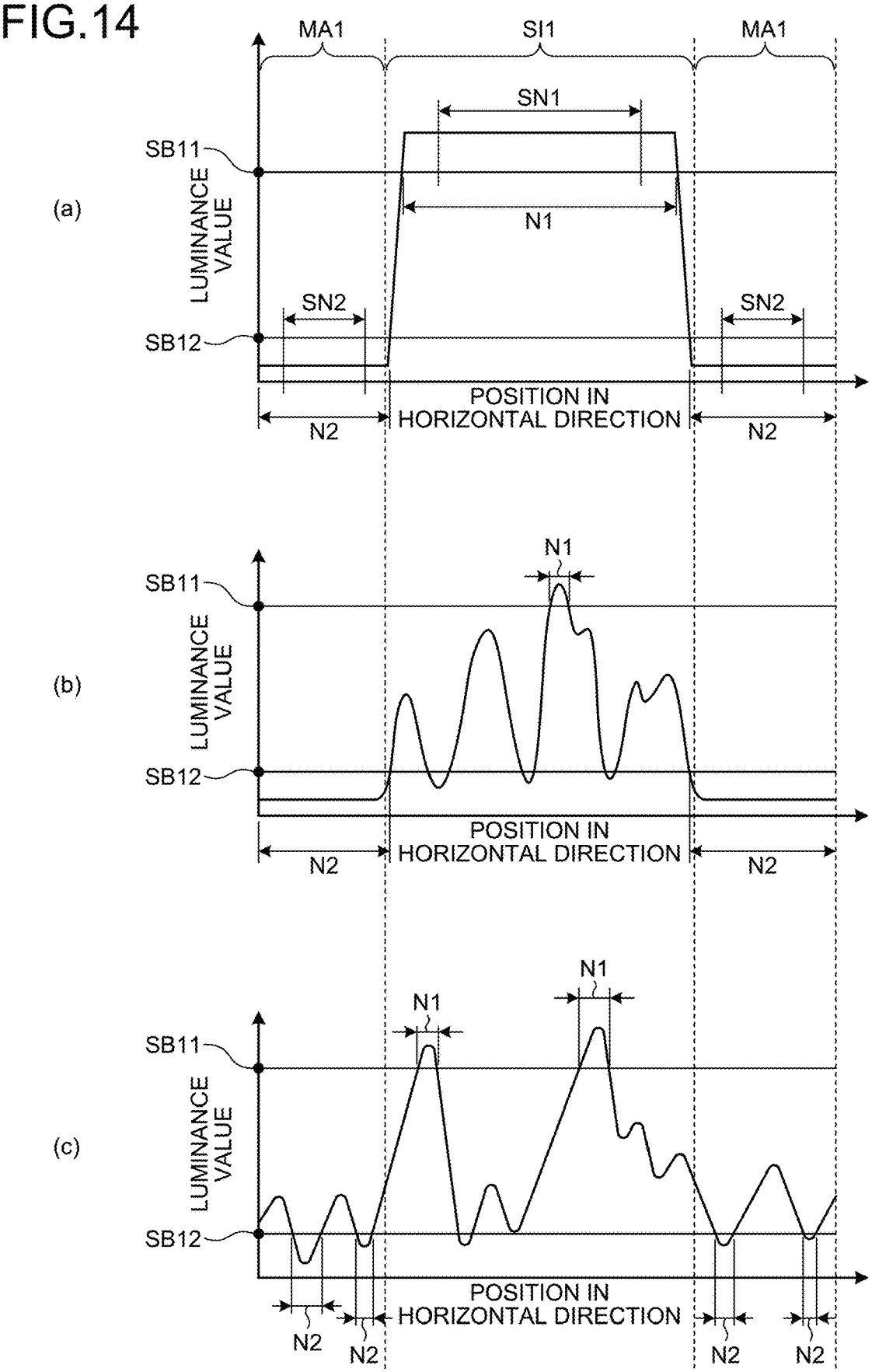
FIG. 14 is a diagram illustrating operations of the endoscope apparatus.

Here, (a) of FIG. 14 illustrates the distribution of the luminance values on the horizontal line L7 in the captured image CI1 in a state where the rigid endoscope 2 is attached to the camera head 5 and a white subject is placed in the field of view of the rigid endoscope 2 in step S1261 (hereinafter referred to as a first state). In the first state, the luminance value of the subject image SI1 is sufficiently high, and the first continuous pixel number N1 is the first pixel number threshold SN1 or more, leading to the determination of the processable state in step S1265.

Furthermore, (b) of FIG. 14 illustrates the distribution of the luminance values on the horizontal line L7 in the captured image CI1 in a state where the rigid endoscope 2 is attached to the camera head 5 but a white subject is not placed in the field of view of the rigid endoscope 2 in step S1261 (hereinafter referred to as a second state). In the second state, the luminance value of the subject image SI1 has large variation, and the first continuous pixel number N1 is less than the first pixel number threshold SN1, leading to the determination of the unprocessable state in step S1265.

Furthermore, (c) of FIG. 14 illustrates the distribution of the luminance values on the horizontal line L7 in the captured image CI1 in a state where the rigid endoscope 2 is not attached to the camera head 5 (hereinafter referred to as a third state). In the third state, since the rigid endoscope 2 is removed from the camera head 5, the variation in the luminance value of the entire captured image CI1 is large. Therefore, similarly to the second state, the first continuous pixel number N1 is less than the first pixel number threshold SN1, leading to the determination of the unprocessable state in step S1265.

When it is determined that the first continuous pixel number N1 is less than the first pixel number threshold SN1 (unprocessable state) (step S1265: No), there is a possibility that the state is either the second or the third state, which means the boundary point BP may not be detected with high accuracy by the mask edge detection process. Accordingly, under the control of the control unit 95, the display controller 96 displays, on the display device 7, a display image obtained by superimposing an image (alert information) including a message such as "Please perform white balance setting operation again" on the captured image CI1 (step S1266). Thereafter, the endoscope apparatus 1 returns to step S1263.

In contrast, when it is determined that the first continuous pixel number N1 is the first pixel number threshold SN1 or more (processable state) (step S1265: Yes), the extraction unit 942 acquires the luminance signal (Y signal) among the image signals (Y, $C_B/C_R$ signals) processed by the image processing unit 92. Subsequently, based on the luminance signal (Y signal), the extraction unit 942 compares the luminance value of each of the pixels on the horizontal line L7 located at the center in the captured image CI1 with the second luminance threshold SB12, and extracts a second pixel having a luminance value lower than the second luminance threshold SB12 (step S1267). Note that step S1267 is constantly executed continuously in parallel with other processes after step S1267.

After step S1267, the processability determination unit 943 compares the second continuous pixel number N2 constituted by the second pixels extracted in step S1267 being continuously arranged on the horizontal line L7 with the second pixel number threshold SN2, and determines whether the second continuous pixel number N2 is the second pixel number threshold SN2 or more (whether the state is a processable state or an unprocessable state) (step S1268). Then, the processability determination unit 943 outputs a signal corresponding to the determination result to the control unit 95.

Here, the rigid endoscope 2 is attached to the camera head 5 in the first and second states. That is, as illustrated in (a) of FIG. 14 or (b) of FIG. 14, the luminance value of the mask area MA1 is sufficiently low, and the second continuous pixel number N2 is the second pixel number threshold SN2 or more, leading to the determination of the processable state in step S1268.

Furthermore, the rigid endoscope 2 is not attached to the camera head 5 in the third state. That is, as illustrated in (c) of FIG. 14, the luminance value of the entire captured image CI1 has a large variation, and the second continuous pixel number N2 is less than the second pixel number threshold SN2, leading to the determination of the unprocessable state in step S1268.

When it is determined that the second continuous pixel number N2 is less than the second pixel number threshold SN2 (unprocessable state) (step S1268: No), there is a possibility that the state is the third state, which means the boundary point BP may not be detected with high accuracy by the mask edge detection process. Therefore, the endoscope apparatus 1 proceeds to step S1266.

In contrast, when it is determined that the second continuous pixel number N2 is the second pixel number threshold SN2 or more (processable state) (step S1268: Yes), the pixel position recognition unit 944 recognizes the pixel position of the second pixel (each of pixel positions of the mask area MA1) at which the second continuous pixel number N2 used in the determination of step S1268 is the second pixel number threshold SN2 or more (step S1269).

After step S1269, the edge detector 941 executes the mask edge detection process (step S1270: mask edge detection step).

After step S1270, the mask width calculation unit 946 calculates the distance between the two boundary points BP located on the horizontal line L7 as the mask width MW1 (step S1271: detection step).

FIG. 15 is a diagram illustrating an example of a captured image when rigid endoscopes 2 having different diameters of insertion portions 22 are connected. Specifically, (a) of FIG. 15 is a diagram illustrating an example of a captured image CI2 captured by the image sensor when the diameter of the insertion portion 22 is smaller than the case of the captured image CI1 illustrated in FIG. 5. (b) of FIG. 15 is a diagram illustrating the distribution of luminance values on a horizontal line L7 in the captured image CI2 illustrated in (a) of FIG. 15. When the diameter of the insertion portion 22 is small, the subject image SI2 is small and the mask area MA2 is expanded as illustrated in FIG. 15. This is because the area having vignetting of the field of view is expanded due to the small diameter of the insertion portion 22. This results in a smaller mask width MW2, which is a distance between the two boundary points BP of the horizontal line L7 in the captured image CI2. A first luminance threshold SB21 and a second luminance threshold SB22 may be the same as or different from the first luminance threshold SB11 and the second luminance threshold SB12, respectively.

After step S1271, the change determination unit 945 determines whether all the pixels at the pixel positions recognized in step S1269 have been continuously extracted as the second pixels by the extraction unit 942 after step S1270 (step S1272). Subsequently, the change determination unit 945 outputs a signal corresponding to the determination result to the control unit 95.

Here, in a case where the mask edge detection process is executed in the first state and then shifts to the second state, the white subject has been simply removed from the distal end of the rigid endoscope 2. Therefore, obviously from comparison between (a) of FIG. 14 and (b) of FIG. 14, there is no change in the luminance value of each of pixels in the mask area MA1. Accordingly, in step S1272, it is determined as "Yes".

In contrast, in a case where the mask edge detection process is executed in the first state and then shift to the third state, the rigid endoscope 2 is removed from the camera head 5, leading to a great amount of variation in the luminance values of the entire captured image CI1. That is, obviously from comparison between (a) of FIG. 14 and (c) of FIG. 14, some pixels at individual pixel positions of the mask area MA1 recognized in the first state are no longer extracted as the second pixel (having the value being the second luminance threshold SB12 or higher). Accordingly, in step S1272, it is determined as "No".

When it is determined that the second pixel has not been continuously extracted (step S1272: No), there is a possibility that the process will shift from the first state to the third state and the rigid endoscope 2 will be replaced with a rigid endoscope 2 different from the rigid endoscope 2 (for example, a rigid endoscope 2 having a different diameter and thus having a different diameter of the subject image SI1 in the captured image CI1). Therefore, the endoscope apparatus 1 proceeds to step S1266.

Meanwhile, in a case where it is determined that the second pixel has been continuously extracted (step S1272: Yes), the endoscope apparatus 1 continues step S1272.

The embodiment described above achieves the following effects. The control unit 95 of the control apparatus 9 according to the embodiment controls the first parameter used for the image processing in the image processing unit 92, such as the digital gain, noise reduction, shading, black level adjustment set value, enhancement, or the like, in accordance with the mask width. As a result, in the endoscope apparatus 1 in which the rigid endoscope 2 is replaceable, it is possible to perform appropriate image processing on the captured image regardless of the type of the rigid endoscope. Furthermore, the control unit 95 controls the second parameter used for controlling the brightness of the captured image CI1 in accordance with the mask width. As a result, in the endoscope apparatus 1 in which the rigid endoscope 2 is replaceable, it is possible to acquire a captured image having an appropriate brightness regardless of the type of the rigid endoscope.

OTHER EMBODIMENTS

While the above is description of the modes for carrying out the present disclosure, the present disclosure should not be limited by only the embodiment described above. In the above-described embodiment, at least a part of the configuration (lens unit 51, lens drive unit 52, lens position detector 53, and imaging unit 54) provided in the camera head 5 may be provided at the distal end of the rigid endoscope 2.

Furthermore, in the above-described embodiment, at least a part of the functions of the control unit 95 may be provided outside the control apparatus 9 (camera head 5, connectors CN1, CN2, or the like). Furthermore, in the above-described embodiment, the input unit that receives various types of operations is not limited to the control apparatus 9, and may be provided in the camera head 5, for example. In the above-described embodiment, the endoscope apparatus 1 may be an endoscope apparatus used in the industrial field for observing the inside of a subject such as a mechanical structure.

Furthermore, in the above-described embodiment, the detection unit 94 detects the mask width, and the control unit 95 controls the first parameter used in the image processing performed by the image processing unit 92, such as the digital gain, noise reduction, shading, black level adjustment set value, enhancement, or the like, and controls the second parameter used for controlling the brightness of the captured image CI1 in accordance with the mask width. Alternatively, the user may input the diameter of the insertion portion 22 of the rigid endoscope 2 into the control apparatus 9, and the control unit 95 may control the first parameter in accordance with the input diameter. Furthermore, the control unit 95 may control the second parameter in accordance with the input diameter. That is, the control apparatus 9 may acquire the diameter of the insertion portion 22 of the rigid endoscope 2 and control the first parameter in accordance with the acquired diameter, or may further control the second parameter.

Although the preferred embodiments of the present disclosure have been described above in detail with reference to the accompanying drawings, the technical scope of the present disclosure is not limited to such examples. It is obvious that a person having ordinary knowledge in the technical field of the present disclosure may come up with various alterations or modifications within the scope of the technical idea described in the claims, and it is naturally to be understood that these should also belong to the technical scope of the present disclosure.

For example, each of devices described herein may be actualized as a single device, or part or all of the devices may be actualized as a separate device. For example, the control apparatus 9, the display device 7, and the medical control apparatus may be actualized as a standalone device. Furthermore, for example, the medical control apparatus may be actualized as a server device connected to the control apparatus 9 and the display device 7 via a network or the like.

Furthermore, the control apparatus 9 described in the present specification may be implemented as a system by having a part or all of individual components actualize as separate devices. For example, the control apparatus 9 may be a system that includes a light source and an imaging device and that actualizes the control unit by an external device.

In addition, the series of processes by individual devices described in the present specification may be implemented by using software, hardware, or a combination of software and hardware. The programs constituting the software are stored in advance in a recording medium or media (non-transitory medium or media) provided inside or outside of the individual devices. In addition, at execution of each of the programs by a computer, for example, the program is loaded to the RAM and executed by a processor such as a CPU.

In addition, the processes described in the present specification using the flowchart and the sequence diagram do not necessarily have to be executed in the order illustrated. Some processing steps may be performed in parallel. Moreover, additional processing steps may be adopted, and some processing steps may be omitted.

Furthermore, the effects described in the present specification are merely illustrative or exemplary, and are not limiting. That is, the techniques according to the present disclosure may have other effects that are apparent to those skilled in the art from the description of the present specification, in addition to or instead of the above effects.

The following configurations also belong to the technical scope of the present disclosure.

(1)

A medical control apparatus to which a rigid endoscope having an insertion portion to be inserted into a subject is detachably connected, the medical control apparatus being configured to perform image processing on a captured image obtained by capturing a subject image introduced by the rigid endoscope and generate a medical photographic image to be displayed on a display device that displays images, the medical control apparatus including:

a detection unit configured to detect a mask width that is a distance between boundary points dividing the subject image included in the captured image and a mask area that is an area other than the subject image; and a control unit configured to calculate a first parameter used for the image processing in accordance with the mask width.

(2)

The medical control apparatus according to (1), wherein the control unit is configured to use the first parameter to perform control such that the smaller the mask width, the greater a digital gain in the image processing.

(3)

The medical control apparatus according to (1) or (2), wherein the control unit is configured to use the first parameter to perform control such that the smaller the mask width, the higher a noise reduction level in the image processing.

(4)

The medical control apparatus according to any one of (1) to (3), wherein the control unit is configured to use the first parameter to perform control such that the smaller the mask width, the higher a shading level in the image processing.

(5)

The medical control apparatus according to any one of (1) to (4), wherein the control unit is configured to use the first parameter to perform control such that the smaller the mask width, the greater a set value of black level adjustment in the image processing.

(6)

The medical control apparatus according to any one of (1) to (5), wherein the control unit is configured to use the first parameter to perform control such that the smaller the mask width, the lower an enhancement level in the image processing.

(7)

The medical control apparatus according to any one of (1) to (6), wherein the control unit is configured to specify a dynamic range of the display device, and calculate the first parameter corresponding to the specified dynamic range of the display device.

(8)

The medical control apparatus according to any one of (1) to (7), wherein the control unit is configured to set a second parameter used for controlling brightness of the captured image in accordance with the mask width.

(9)

The medical control apparatus according to (8), wherein the control unit is configured to use the second parameter to perform control such that the smaller the mask width, the greater an analog gain in signal processing in an imaging unit.

(10)

The medical control apparatus according to (8) or (9), wherein the control unit is configured to use the second parameter to perform control such that the smaller the mask width, the longer an exposure time for each of pixels of an image sensor included in an imaging unit.

(11)

The medical control apparatus according to any one of (8) to (10), wherein the control unit is configured to use the second parameter to perform control such that the smaller the mask width, the larger the amount of light supplied from a light source device to the insertion portion.

(12)

The medical control apparatus according to any one of (8) to (11), wherein the control unit is configured to specify a dynamic range of the display device, and calculate the second parameter corresponding to the specified dynamic range of the display device.

(13)

A method of controlling a medical control apparatus to which a rigid endoscope having an insertion portion to be inserted into a subject is detachably connected, the medical control apparatus being configured to perform image processing on a captured image obtained by capturing a subject image introduced by the rigid endoscope and generate a medical photographic image to be displayed on a display device that displays images, the method including:

detecting a mask width being a distance between boundary points dividing the subject image included in the captured image and a mask area being an area other than the subject image; and calculating a first parameter used for the image processing in accordance with the mask width.

(14)

A method of controlling a medical control apparatus to which a rigid endoscope having an insertion portion to be inserted into a subject is detachably connected, the medical control apparatus being configured to perform image processing on a captured image obtained by capturing a subject image introduced by the rigid endoscope and generate a medical photographic image to be displayed on a display device that displays images, the method including:

acquiring a diameter of the insertion portion; and calculating a first parameter used for the image processing in accordance with the diameter of the insertion portion.

As described above, according to the present disclosure, in an endoscope apparatus in which a rigid endoscope is exchangeable, it is possible to achieve a medical control apparatus and a method of controlling a medical control apparatus capable of applying appropriate image processing on a captured image regardless of the type of the rigid endoscope. Note that the above effects are not necessarily limited, and any of the effects illustrated in the present specification or other effects that may be grasped from the present specification may be obtained in addition to or in place of the above effects.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control apparatus to which an endoscope having an insertion portion to be inserted into a subject is detachably connected, the medical control apparatus being configured to perform image processing on a captured image obtained by capturing a subject image introduced by the endoscope and generate a medical photographic image to be displayed on a display device that displays images, the medical control apparatus comprising:
a control circuit configured to
acquire a mask width that is a distance between boundary points dividing the subject image included in the captured image and a mask area that is an area other than the subject image,
calculate a first parameter used for the image processing in accordance with the mask width, and
use the first parameter to perform control such that the smaller the mask width, at least one of
the greater a digital gain in the image processing,
the higher a noise reduction level in the image processing,
the higher a shading level in the image processing,
the greater a set value of black level adjustment in the image processing, and
the lower an enhancement level in the image processing.

2. The medical control apparatus according to claim 1, wherein the control circuit is configured to use the first parameter to perform control such that the smaller the mask width, the greater a digital gain in the image processing.

3. The medical control apparatus according to claim 1, wherein the control circuit is configured to use the first parameter to perform control such that the smaller the mask width, the higher a noise reduction level in the image processing.

4. The medical control apparatus according to claim 1, wherein the control circuit is configured to use the first parameter to perform control such that the smaller the mask width, the higher a shading level in the image processing.

5. The medical control apparatus according to claim 1, wherein the control circuit is configured to use the first parameter to perform control such that the smaller the mask width, the greater a set value of black level adjustment in the image processing.

6. The medical control apparatus according to claim 1, wherein the control circuit is configured to use the first parameter to perform control such that the smaller the mask width, the lower an enhancement level in the image processing.

7. The medical control apparatus according to claim 1, wherein the control circuit is configured to
specify a dynamic range of the display device, and
calculate the first parameter corresponding to the specified dynamic range of the display device.

8. The medical control apparatus according to claim 1, wherein the control circuit is configured to set a second parameter used for controlling brightness of the captured image in accordance with the mask width.

9. The medical control apparatus according to claim 8, wherein the control circuit is configured to use the second parameter to perform control such that the smaller the mask width, the greater an analog gain in signal processing in an image sensor.

10. The medical control apparatus according to claim 8, wherein the control circuit is configured to use the second parameter to perform control such that the smaller the mask width, the longer an exposure time for each of pixels of an image sensor.

11. The medical control apparatus according to claim 8, wherein the control circuit is configured to use the second parameter to perform control such that the smaller the mask width, the larger the amount of light supplied from a light source device to the insertion portion.

12. The medical control apparatus according to claim 8, wherein the control circuit is configured to
specify a dynamic range of the display device, and
calculate the second parameter corresponding to the specified dynamic range of the display device.

13. A method of controlling a medical control apparatus to which an endoscope having an insertion portion to be inserted into a subject is detachably connected, the medical control apparatus being configured to perform image processing on a captured image obtained by capturing a subject image introduced by the endoscope and generate a medical photographic image to be displayed on a display device that displays images, the method comprising:
detecting a mask width being a distance between boundary points dividing the subject image included in the captured image and a mask area being an area other than the subject image;
calculating a first parameter used for the image processing in accordance with the mask width; and
using the first parameter to perform control such that the smaller the mask width, at least one of
the treater a digital lain in the image processing,
the higher a noise reduction level in the image processing,
the higher a shading level in the image processing,
the greater a set value of black level adjustment in the image processing, and
the lower an enhancement level in the image processing.

14. A method of controlling a medical control apparatus to which an endoscope having an insertion portion to be inserted into a subject is detachably connected, the medical control apparatus being configured to perform image processing on a captured image obtained by capturing a subject image introduced by the endoscope and generate a medical photographic image to be displayed on a display device that displays images, the method comprising:

acquiring a diameter of the insertion portion;

calculating a first parameter used for the image processing in accordance with the diameter of the insertion portion; and setting a second parameter used for controlling brightness of the captured image in accordance with the diameter of the insertion portion.

15. A medical control apparatus to which an endoscope having an insertion portion to be inserted into a subject is detachably connected, the medical control apparatus being configured to perform image processing on a captured image obtained by capturing a subject image introduced by the endoscope and generate a medical photographic image to be displayed on a display device that displays images, the medical control apparatus comprising:

a control circuit configured to acquire a mask width that is a distance between boundary points dividing the subject image included in the captured image and a mask area that is an area other than the subject image, calculate a first parameter used for the image processing in accordance with the mask width, and set a second parameter used for controlling brightness of the captured image in accordance with the mask width.

16. The medical control apparatus according to claim 15, wherein the control circuit is configured to use the second parameter to perform control such that the smaller the mask width, the greater an analog gain in signal processing in an image sensor.

17. The medical control apparatus according to claim 15, wherein the control circuit is configured to use the second parameter to perform control such that the smaller the mask width, the longer an exposure time for each of pixels of an image sensor.

18. The medical control apparatus according to claim 15, wherein the control circuit is configured to use the second parameter to perform control such that the smaller the mask width, the larger the amount of light supplied from a light source to the insertion portion.

19. The medical control apparatus according to claim 15, wherein the control circuit is configured to specify a dynamic range of the display device, and calculate the second parameter corresponding to the specified dynamic range of the display device.

20. The medical control apparatus according to claim 15, wherein the control circuit is configured to use the first parameter to perform alter image processing parameters based on the mask width.

* * * * *